US005149650A

United States Patent [19]

Wertz et al.

[11] Patent Number: 5,149,650

[45] Date of Patent: Sep. 22, 1992

[54] VACCINES FOR HUMAN RESPIRATORY VIRUS

[75] Inventors: Gail W. Wertz, Birmingham, Ala.; Peter L. Collins, Rockville, Md.

[73] Assignee: University of North Carolina at Chapel Hill, Chapel Hill, N.C.

[21] Appl. No.: 218,737

[22] Filed: Jul. 13, 1988

Related U.S. Application Data

[63] Continuation-in-part of PCT/US86/02756, Dec. 23, 1986/which is a continuation in-part of Ser. No. 818,740, Jan. 14, 1986, abandoned.

[51] Int. Cl.[5] .............................................. C12N 1/00
[52] U.S. Cl. .............................................. 435/243
[58] Field of Search .............................................. 435/243

[56] References Cited

U.S. PATENT DOCUMENTS

| | | | |
|---|---|---|---|
| 4,122,167 | 10/1978 | Buynak et al. | 424/89 |
| 4,145,252 | 3/1979 | Buynak et al. | 435/237 |
| 4,517,304 | 5/1985 | Stott | 436/518 |
| 4,743,553 | 5/1988 | Rice | 435/253 |

OTHER PUBLICATIONS

Chemical Abstracts CA90(19)148263 (s).
Collins, P. L. et al., Identification of a Tenth mRNA of Respiratory Syncytial Virus and Assignment of Polypeptides to the 10 Viral Genes, J. of Virology, 49(No. 2):572-578 (Feb. 1984).
Friedewald, W. T. et al., Low-Temperature-Grown RS Virus in Adult Volunters, J. of Amer. Med. Assoc., 204(No. 8):690-694 (May 20, 1968).
Kim, H. W. et al., Clinical and Immunological Response of Infants and Children to Administration of Low-Temperature Adapted Respiratory Syncytial Virus, Pediatrics, 48(No. 5):745-755 (Nov. 1971).
McIntosh, K. et al., Attenuated Respiratory Syncytial Virus Vaccines in Asthmatic Children, Pediatric Res., 8:689-696 (1974).
Craighead, J. E., Report of a Workshop: Disease Accentuation after Immunication with Inactivated Microbial Vaccines, J. of Infectious Dis., 131(No. 6):749-753 (Jun. 1975).
Wright, P. F. et al., Evaluation of a live, attenuated respiratory syncytial virus vaccine in infants, J. of Pediatrics, 88(No. 6):931-936 (Jun. 1976).
Raeburn, P., The Houdini Virus, Science 85, 6:52-57 (Dec. 1985).
Collins, P. L. et al., Nucleotide sequence of the gene encoding the fusion (F) glycoprotein of human respiratory syncytial virus, Proc. Natl. Acad. Sci., USA, 81:7683-7687 (Dec. 1984).
Collins, P. L. et al., The 1A Protein Gene of Human Respiratory Syncytial Virus: Nucleotide Sequence of the mRNA and a Related Polycistronic Transcript, Virology, 141:283-291 (1985).
Collins, P. L. and Wertz, G. W., The Envelope-Associated 22K Protein of Human Respiratory Syncytial Virus: Nucleotide Sequence of the mRNA and a Related Polytranscript, J. of Virology, 54(No. 1):65-71 (Apr. 1985).
Collins, P. L. et al., Correct Sequence for the Major Nucleocapsid Protein mRNA of Respiratory Syncytial Virus, Virology, 146:69-77 (1985).
Collins, P. L. et al., Nucleotide sequence of the gene encoding the fusion (F) glycoprotein of human respiratory syncytial virus, Proc. Natl. Acad. Sci., USA, 81:7683-7687 (Dec. 1984).
Ball, L. A. et al., Expression of the major glycoprotein G of human respiratory syncytial virus from recombinant vaccinia virus vectors, Proc. Natl. Acad. Sci., USA, 83:246-250 (Jan. 1986).
Olmsted, R. A. et al., Expression of the F glycoprotein of respiratory syncytial virus by a recombinant vaccinia virus: Comparison of the individual contributions of the F and G glycoproteins to host immunity, Proc. Natl. Acad. Sci., USA, 83:7462-7466 (Oct. 1986).
Stott, E. J. and Taylor, G., Respiratory Syncytial Virus, Brief Review, Archives of Virology, 84:1-52 (1985).
Stott, E. J. et al., Human Respiratory Syncytial Virus Glycoprotein G Expressed from Recombinant Vaccinia Virus Vector Protects Mice Against Live-virus Challenge, J. of Virology 67:607-613 (1986).
Elango, N. et al., Resistance to human respiratory syncytial virus (RSV) infection induced by immunization of cotton rats with a recombinant vaccinia virus expressing the RSV G glycoprotein, Proc. Natl. Acad. Sci., USA, 83:1906-1910 (Mar. 1986).

*Primary Examiner*—Paul J. Killos
*Attorney, Agent, or Firm*—Mark DeLuca; Ruth H. Newtson; Kenneth A. Weber

[57] ABSTRACT

This invention discloses compositions of DNA and proteins that are useful for preparing vaccines against human respiratory syncytial virus [HRSV]. The DNA compositions include structural genes coding for native structural viral proteins and immunogenic fragments of these proteins. Host cells transformed with the above DNA compositions are also disclosed. Vaccines made from the native structural viral proteins or immunogenic fragments are also disclosed as well as methods for protecting humans by inoculation with these vaccines.

26 Claims, No Drawings

VACCINES FOR HUMAN RESPIRATORY VIRUS

CROSS REFERENCE TO RELATED APPLICATIONS

This application is a continuation in part of International Patent Application Number PCT/US86/02756, filed 23 Dec. 1986, which is a continuation-in-part of U.S. patent application Ser. No. 818,740, filed 14 Jan. 1986, abandoned.

FIELD OF THE INVENTION

This invention discloses compositions of DNA and proteins that are useful for preparing vaccines against human respiratory syncytial virus [HRSV]. The DNA compositions include structural genes coding for native structural viral proteins and immunogenic fragments of these proteins. Host cells transformed with the above DNA compositions are also disclosed. Vaccines made from the native structural viral proteins or immunogenic fragments are also disclosed as well as methods for protecting humans by inoculation with these vaccines. This invention was made with Government support under At-12464 awarded by the National Institute of Health. The Government has certain rights in the invention.

BACKGROUND OF THE INVENTION

HRSV was first discovered in 1956 and is worldwide in distribution. It is an important cause of upper and lower respiratory tract disease causing illness in infants and young children. In infants this severe illness often requires hospitalization. About 30 percent of hospitalized young children with acute respiratory disease have respiratory syncytial virus infection. In older children and adults the disease is milder. Infections with respiratory syncytial virus are referable to all segments of the respiratory tract, are usually associated with fever, cough, runny nose, and fatigue, and are diagnosed clinically as bronchitis, bronchiolitis, pneumonia, croup, or viral infection. In older children and adults and virus is generally limited to replication in the upper respiratory tract. Infants may be more severely involved when the virus extends into the lungs. Lung damage can be permanent.

Primary infection with respiratory syncytial virus occurs early in life, usually before 4 year of age. Among children, illness caused by this virus tends to occur at least once each year in rather sharply defined outbreaks of several months duration. Epidemics are sharply circumscribed, generally for 3 to 5 months. In family studies, children in early school years frequently introduce the virus into the home, infecting younger members of the family more severely than other family members. The clinical consequence of infection is most severe on first experience and becomes milder in older individuals who are immunologically experienced.

The effects of respiratory syncytial virus can range from unapparent infection to severe pneumonia and death. Inflammation of the respiratory track is responsible for most symptoms. Complete recovery in most cases occurs in one to three weeks with the production of antibody which appears to persist throughout life. In the United States about 30 percent of one year old infants and 95 percent of five year old children have circulating respiratory syncytial virus antibody. Reinfections in older infants, children, and adults with antibody are mostly mild upper respiratory illnesses in the form of cords.

With exception of the present invention, there are no effective vaccines to combat HRSV.

INFORMATION DISCLOSURE STATEMENT

Although low yields of virus in cell culture have hindered HRSV research, the virus has been well studied. HRSV is a paramyxovirus containing a single negative strand of RNA which is transcribed into 10 predominantly monocistronic messengers. The messengers have been isolated and translated in vitro. The products have been characterized by gel electrophoresis, peptide mapping and immuno-precipitation as being similar to structural proteins isolated from virions.

The structural proteins include a major nucleocapsid protein (N; MW ca. 42,000), a nucleocapsid phosphoprotein (P; MW ca. 34,000), a large nucleocapsid protein (L; MW ca. 200,000), an envelope matrix protein (M; MW ca. 26,000), a matrix glycoprotein (ca. 22,000) and two envelope glycoproteins, a fusion glycoprotein (F; MW ca. 68,000 to 70,000) and a methioninepoor glycoprotein (G; MW ca. 84,000 to 90,000). In addition, a viral encoded protein of about 9,500 daltons and other small proteins are known to be present in infected cells; Collins, P. L. et al, Identification of a Tenth mRNA of RSV and Assignment of Polypeptides to the 10 Viral Gene, J. of Virol. 49:572-578 (1984) and references cited therein. Although the structural proteins of HRSV have been isolated, their amino acid sequences are not known.

Multiple attempts have been made to obtain an effective vaccine against HRSV. Friedewald et al., Journal of the American Medical Association, Vol. 204:690-694 (20 May 1968), describe the propagation of respiratory syncytial virus in bovine embryonic kidney tissue culture. Virus grown at 34° C. or 28° C. did not decrease in infectivity or virulence. HRSV grown at 26° C., while associated with a decrease in infectivity for adults, could not be considered for use in prevention of infection in adults since the virus had limited infectivity and was poorly immunogenic.

Kim et al., Pediatrics, 48:745-755 (Nov. 1971), disclose that inactivated respiratory syncytial virus vaccine prepared from virus grown at 26° C. stimulated the development of high levels of serum antibody in infants and children from 6 months to 13 years in age but did not present infection.

McIntosh et al., Pediatric Research, 8:689-696 (1974), discuss two experimental live respiratory syncytial virus vaccines, one prepared from virus grown at 26° C. and the other, prepared from a temperature sensitive mutant which grew well at 32° C. and not at all at 37° C. or higher. The first vaccine was unsatisfactory as it did not protect against infection when the interval between vaccination and challenge was greater than 4 months. The second vaccine was also unsatisfactory in that it apparently lost its temperature sensitivity in some vaccines.

Craighead, Journal of Infectious Diseases, 131:749-753 (Jun. 1975), discusses tests conducted in 1966 wherein several groups of investigators tested in infants and young children a formaldehyde-treated, alum-precipitated virus grown in tissue culture. Upon subsequent exposure to wild virus the vaccine recipients exhibited an accentuated pattern of respiratory tract disease. Craighead concludes that immunization with formaldehyde treated virus enhanced the severity of the disease.

Wright et al., Journal of Pediatrics, 88:931-936 (Jun. 1976), describe the evaluation in infants of a temperature sensitive live attenuated respiratory syncytial vaccine. While this vaccine when administered at a dosage level sufficiently high to infect all seronegative infants caused mild upper respiratory illness, lowering the dose did not achieve an acceptable level of infectivity. The virus was also genetically unstable as there was evidence of loss of temperature sensitivity in one vaccinee. There was no evidence for potentiation of natural illness with this vaccine and reinfection occurred among vaccinees.

U.S. Pat. Nos. 4,122,167 and 4,145,252 describe a method for attenuating virions by serial passage through human diploid lung fibroblasts and U.S. Pat. No. 4,517,304 discloses a method for producing immunogenically active HRSV proteins upon the cell membranes of susceptible cells grown in culture. These cells are then injected into a host to elicit an immune response.

None of the above references disclose the methods or compositions disclosed in this invention. The above references attempt to create a vaccine by injection of virions comprised of both protein and nucleic acid or by injection of undefined compositions of virus proteins attached to the cell membrane of host cells. None of the above work has resulted in an effective vaccine. Raeburn, P., The Houdini Virus, Science 85, 6:52-57 (Dec. 1985). Disclosed herein are compositions of pure viral protein and methods for producing commercially practical amounts of that protein. The viral proteins are useful for producing vaccines, antibodies for diagnostics, and the clones carrying the HRSV-like cDNA can also be used for diagnostic purposes. Moreover, vaccines produced from the proteins can be tailored to contain any proportion of the structural proteins that will best afford immuno-protection. This invention avoids the exposure of young children to intact HRSV virions either inactivated or attenuated and to viral nucleic acid. By avoiding the injection of a complete virion, the vaccines disclosed herein need not be treated with a fixative such as formaldehyde which has been shown to result in the development of ineffective antibodies and in the subsequent increased susceptibility of the host/patient when exposed to virulent HRSV.

The following references by the inventors of this invention are offered to complete the relevant HRSV literature, but are not prior art references under 35 U.S.C. 102(b): Collins, P. L. et al., Nucleotide Sequence of the gene encoding the fusion (F) glycoprotein of human respiratory syncytial virus, Proc. Natl. Acad. Sci., USA, 81:7683-7687 (Dec. 1984) disclosing the gene sequence for the F glycoprotein; Collins, P. L. et al., The 1A Protein Gene of Human Respiratory Syncytial Virus: Nucleotide Sequence of the mRNA and a Related Polycistronic Transcript, Virology, 141:283-291 (1985) disclosing the gene sequence for the 1A protein; Collins, P. L. et al., The Envelope-Associated 22K Protein of Human Respiratory Syncytial Virus: Nucleotide Sequence of the mRNA and a Related Polytranscript, J. of Virol., 54(No. 1):65-71 (Apr. 1985) disclosing the gene sequence for the 22K protein; Wertz, G. W. et al., Nucleotide sequence of the G protein gene of human respiratory syncytial virus reveals an unusual type of viral membrane protein, Proc. Natl. Acad. Sci., USA, 82:4075-4079 (Jun. 1985) disclosing the gene sequence for the G glycoprotein; and Collins, P. L. et al., Correct Sequence for the Major Nucleocapsid Protein mRNA of Respiratory Syncytial Virus, Virology, 146:69-77 (1985) disclosing the gene sequence for the N protein.

In 1986, it was demonstrated that the vaccinia virus expression system was useful for expressing the G and F glycoproteins of HRSV. Ball, L. A., et al, Expression of the Major Glycoprotein G of Human Respiratory Syncytial Virus from Recombinant Vaccinia Virus Vectors, P.N.A.S. USA 83:246-250 (1986) and Olmsted, R. A., Expression of the F Glycoprotein of Respiratory Syncytial Virus by a Recombinant Vaccinia Virus: Comparison of the Individual Contributions of the F and G Glycoproteins to Host Immunity, P.N.A.S. USA 83:7462-7466 (1986). These two glycoproteins were also demonstrated to induce immunoprotection in mammals against a live HRSV virus challenge. Stott, E. J., Human Respiratory Syncytial Virus Glycoprotein G Expressed from Recombinant Vaccinia Virus Vector Protects Mice Against Live-virus Challenge, Journal of Virology 67:607-613 (1986); Elango N., et al., Resistance and Human Respiratory Syncytial Virus (RSV) Infection Induced by Immunization of Cotton Rats with a Recombinant Vaccinia Virus Expressing the RSV G Glycoprotein; and, Olmsted, R. A. (supra) P.N.A.S. USA 83:246-250 (1986). The methodology and results of the above references are all incorporated by reference herein.

SUMMARY OF THE INVENTION

This invention discloses a DNA sequence coding for human respiratory syncytial virus structural proteins selected from the group consisting of F protein, G protein, 22K protein, 9.5K protein, N protein and immunogenic fragments thereof. Most preferred are the G and F glycoproteins and immunogenic fragments thereof.

This invention discloses compositions of DNA sequences coding for the above HRSV structural proteins or immunogenic fragments wherein the sequence is recombined into a plasmid capable of independent replication in a suitable host, of incorporation into the host genome or of inducing expression of the DNA sequences coding for viral proteins or immunogenic fragments in a suitable host. Suitable hosts include bacteria, yeast and eukaryote cell cultures.

This invention also discloses compositions of essentially pure protein selected from the group of HRSV structural proteins consisting of F protein, G protein, 22K protein, 9.5K protein, N protein and immunogenic fragments thereof.

Vaccines and methods of using the vaccines are disclosed herein in which the vaccine is comprised of a polypeptide selected from the group of HRSV structural proteins consisting of F protein, G protein, 22K protein, 9.5K protein, N protein and immunogenic fragments thereof. Most preferred are the F protein, G protein and immunogenic fragments thereof.

DETAILED DESCRIPTION OF THE INVENTION

This invention involves a series of molecular genetic manipulations that can be achieved in a variety of known ways. The following descriptions will detail the various methods available to express the HRSV proteins and are followed by specific examples of preferred methods. The manipulations can be described as the obtaining of a cDNA of HRSV proteins, the cloning and replication of the cDNA in *E. coli* and the expression of the desired cDNA in a suitable host.

The specific sequence and base numbering positions for the disclosed proteins of HRSV strain $A_2$ are illustrated in Charts 12-16. Charts 12-16 contain the nucleic acid sequences for HRSV structural proteins F protein, G protein, 22K protein, 9.5K protein, and N protein.

It is anticipated that protein from the $A_2$ strain will induce cross-protection against other strains of HRSV; however, it is possible that maximum protection will involve immunization with a mixture of proteins from various strains.

A. General Methods

The nomenclature and general laboratory procedures required in this application can be found in Maniatis, T. et al., Molecular Cloning A Laboratory Manual, Cold Spring Harbor Laboratory, Cold Spring Harbor, N.Y., 1982. The manual is hereinafter referred to as Maniatis.

All *E. coli* strains are grown on Luria broth (LB) with glucose, Difco's Antibiotic Medium #2 and M9 medium supplemented with glucose and acid-hydrolyzed casein amino acids. Strains with resistance to antibiotics were maintained at the drug concentrations described in Maniatis. Transformations were performed according to the method described by Rowekamp, W. and Firtel, R. A., Dev. Biol., 79:409-418 (1980).

All enzymes were used according to the manufacturer's instructions. Transformants were analyzed by colony hybridization as described in Grunstein, M. and Wallis, J., Methods in Enzymology, 68:379-388.

After hybridization, the probes are removed and saved, and the filters are washed in 0.1% SDS, 0.2x SSC for a total of 3 hours with 5 changes of 400 ml each. Filters are thoroughly air dried, mounted, and autoradiographed using Kodak X-OMAT AR film and Dupont Cronex Lightening Plus intensifying screens for 16 hours at −70° C.

For sequencing of plasmids, purified plasmid DNA is prepared according to the methods described in Maniatis. End-labeled DNA fragments are prepared and analyzed by the chemical sequencing methods of Maxam and Gilbert with modifications described by Collins, P. L. and Wertz, G. W., J. Virol. 54:65-71 (1985).

Nucleotide sizes are given in either kilobases (kb) or basepairs (bp). These are estimates derived from agarose gel electrophoresis.

B. HRSV cDNA

The first step in obtaining expression of HRSV proteins is to obtain the DNA sequence coding for the protein from cDNA clones. This sequence is then cloned into an expression plasmid which is capable of directing transcription of the gene and allowing efficient translation of the transcript. The library method for obtaining cDNA encoding HRSV proteins has been described generally in Maniatis, T., Fritsh, E. F., and Sambrook, J. (1982). Molecular Cloning, A Laboratory Manual, Cold Spring Harbor Laboratory, New York and specifically in Collins, P. L. and Wertz, G. W., cDNA Cloning and Transcriptional Mapping of Nine Polyadenylated RNAs Encoded by the Genome of HRSV, Proc. Natl. Acad. USA 80:3208-3212 (1983).

Clones are prepared by inserting the cDNA into PstI cleaved pBR322 to which homopolymer tracts of dGTP have been enzymatically added to the 3'ends at the cleavage site. Homopolymer tracts of dCTP are enzymatically added to the 3′ termini of the cDNA molecules according to the methods described by Maniatis. Ideally, 10-30 residues of dCTP or dGTP should be added to maximize cloning efficiency. The cDNA and plasmid are annealed together and transformed into *E. coli.* The clones containing full length HRSV cDNA are detected by probes of labeled viral cDNA or oligonucleotides complementary to portions of the sequences illustrated in Charts 12-16, followed by restriction enzyme analysis and DNA sequencing.

Oligonucleotides are chemically synthesized according to the solid phase phosphoramidite triester method first described by Beaucage S. L. and Caruthers, M. H. Tetrahedron Letts. 22(20):1859-1862 (1981) using an automated synthesizer, as described in Needham-VanDevanter, D. R., et al., Nucleic Acids Res., 12:6159-6168 (1984). Purification of oligonucleotides is by either native acrylamide gel electrophoresis or by anion-exchange HPLC as described in Pearson, J. D. and Regnier, F. E., J. Chrom., 255:137-149 (1983). The sequence of the synthetic oligonucleotides can be verified using the chemical degradation method of Maxam, A. M. and Gilbert, W., Grossman, L. and Moldave, D., eds., Academic Press, New York, Methods in Enzymology, 65:499-560 (1980).

C. Expression in *E. coli*

To obtain high level expression of a cloned gene in a prokaryotic system, it is essential to construct expression vectors which contain a strong promoter to direct mRNA transcription, a ribosome binding site for translational initiation, and a transcription terminator. Examples of regulatory regions suitable for this purpose are the promoter and operator region of the *E. coli* tryptophan biosynthetic pathway as described by Yanofsky, C., Kelley, R. L. and Horn, V., J. Bacteriol., 158:1018-1024 (1984) and the leftward promoter of phage lambda ($P_L$) as described by Herskowitz, I. and Hagen, D., Ann. Rev. Genet., 14:399-445 (1980).

HRSV-like proteins produced in *E. coli* will not fold properly due to the presence of cysteine residues and to the lack of suitable post-translational modifications. During purification from *E. coli,* the expressed proteins must first be denatured and the renatured. This can be accomplished by solubilizing the *E. coli* produced proteins in guanidine HCl and reducing all the cysteine residues with $\beta$-mercaptoethanol. The protein is then renatured either by slow dialysis or by gel filtration.

Detection of HRSV-like proteins is achieved by methods known in the art such as radioimmunoassays, or Western blotting techniques or immunoprecipitation. Purification from *E. coli* can be achieved following procedures described in U.S. Pat. No. 4,511,503.

D. Expression of HRSV-like proteins in Yeast

Expression of heterologous proteins in yeast is well known and described. Methods in Yeast Genetics, Sherman, F., et al., Cold Spring Harbor Laboratory, (1982) is a well recognized work describing the various methods used to produce HRSV-like proteins in yeast. For high level expression of a gene in yeast, it is essential to connect the gene to a strong promoter system and provide efficient transcription termination/polyadenylation sequences from a yeast gene. Examples of useful promoters include GAL1,10 (Johnston M., and Davis, R. W., Mol. and Cell. Biol., 4:1440-48, 1984), ADH2 (Russell, D., et al., J. Biol. Chem. 258:2674-2682, 1983), PHO5 (EMBOJ. 6:675-680, 1982), and MF$\alpha$1. A multicopy plasmid with a selective marker such as Lue-2, URA-3, Trp-1, and His-3 is also desirable. The MF=1 promoter is preferred. The MFα1 promoter, in a host of the α mating-type is constitutive, but is off in diploids or cells with the a mating-type. It can be regulated by raising or lowering temperature in hosts which have a ts mutation at one of the SIR loci. The effect of such a mutation at 35° C. on an α type cell is to turn on the normally silent gene coding for the a mating-type. The expression of the silent a mating-type gene, in turn, turns off the MFα1 promoter. Lowering the temperature of growth to 27° C. reverses the process, Herskowitz, I. & Oshima, Y., The Molecular Biology of the Yeast Saccharomyces, eds. Strathern, J. N., Jones, E. W., Broach, J. R., Cold Spring Harbor Lab., Cold Spring Harbor, N.Y., pp 181-209 (1982). The polyadenylation sequences are provided by the 3'-end sequences of any of the highly expressed genes, like ADH1, MFα1, or TPI, Alber, T. and Kawasaki, G., J. of Mol. & Appl. Genet. 1:419-434 (1982). A number of yeast expression plasmids like YEp6, YEp13, YEp24 can be used as vectors. A gene of interest such as HRSV-like protein cDNA can be fused to any of the promoters mentioned above, and then ligated to the plasmids for expression in various yeast hosts. The above mentioned plasmids have been fully described in the literature, Botstein, et al., Gene, 8:17-24 (1979); Broach, et al., Gene, 8:121-133 (1979).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, Nature (London), 275:104-109 (1978); and Hinnen, A., et al., Proc. Natl. Acad. Sci. USA, 75:1929-1933 (1978). The second procedure does not involve removal of the cell wall. Instead the cells are treated with lithium-chloride or acetate and PEG and put on selective plates, Ito, H. et al., J. Bact., 153:163-168 (1983).

HRSV-like proteins can be isolated from yeast by lysing the cells and applying standard protein isolation techniques to the lysates. The proteins can be detected by using Western blot techniques or radioimmunoassays.

E. Expression in Cell Cultures

The HRSV cDNA can be ligated to various expression vectors for use in transforming host cell cultures. The vectors all contain gene sequences to initiate transcription and translation of the HRSV-like proteins that are compatible with the host cell to be transformed. In addition, the vectors preferably contain a marker to provide a phenotypic trait for selection of transformed host cells such as dihydrofolate reductase or metallothionein. Additionally a replicating vector might contain a replicon.

Illustrative of cell cultures useful for the production of HRSV-like proteins are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above, the vector which is used to transform the host cell preferably contains gene sequences to initiate the transcription and translation of the HRSV-like proteins gene sequence. These sequences are referred to as expression control sequences. When the host cell is of mammalian or insect origin illustrative useful expression control sequences are obtained from the SV-40 promoter, Science, 222:524-527 (1983), the CMV I.E. promoter, Proc. Natl. Acad. Sci., 81:659-663 (1984), the metallothionein promoter, Nature, 296:39-42 (1982) or the baculovirus polyhedrin promoter, Virol., 131:561-565 (1983). The plasmid or replicating or integrating DNA material containing the expression control sequences is cleaved using restriction enzymes and adjusted in size as necessary or desirable and ligated with cDNA coding for HRSV-like proteins by means well known in the art. As with yeast when higher animal host cells are employed, polyadenylation or transcription terminator sequences from known mammalian genes need to be incorporated into the vector. An example of a terminator sequence is the polyadenylation sequence from the bovine growth hormone gene.

The HRSV glycoprotein F may be designed to be secreted from cells into the surrounding media. This is accomplished by causing the early termination of the glycoprotein prior to its anchor region. Lasky et al., Biotechnology, 2:527-532 (1984). The anchor is a hydrophobic region at the carboxy terminal end of the glycoprotein which causes the retention of the glycoprotein in the cell membrane. Early termination may be accomplished by inserting a universal translational terminator oligonucleotide into an appropriate site in the gene's DNA. These oligonucleotides are commercially available. For the F gene, a preferred site for insertion is the NsiI restriction enzyme site which is approximately 1.5 kb from the 5' end of the gene. Additionally, gene sequences to control replication in the host cell may be incorporated into the vector such as those found in bovine papillomavirus type-vectors, Saveria-Campo, M., Bovine Papillomavirus DNA: A Eukaryotic Cloning Vector, DNA Cloning Vol II A Practical Approach, ed. D. M. Glover, IRL Press, Arlington, Va., p. 213-238 (1985).

The preferred expression vector useful for expressing HRSV-like proteins in Chinese hamster ovary (CHO) cell is a shuttle vector pSVCOW7 which replicates in both CHO and *E. coli* cells utilizing ampicillin resistance and dihydrofolate reductase genes as markers in *E. coli* and CHO cells respectively. Plasmid pSVCOW7 also provides the polyadenylation sequence from bovine growth hormone which is necessary for expression in CHO cells. Plasmid pSVCOW7 is cleaved and a viral promoter and the HRSV-like protein cDNAs inserted.

The preferred expression vector useful in forming recombinant baculovirus for expressing HRSV-like proteins in insect cells is pAc373. Smith et al., Mol. Cell. Biol. 3:2156-2165 (1983). The plasmid replicates in *E. coli* cells utilizing ampicillin resistance, and provides the eukaryotic promoter and polyadenylation signal from the baculovirus polyhedrin gene for expression of HRSV genes. Plasmid pAc373 is cleaved and a HRSV cDNA is inserted adjacent to the promoter. This new plasmid is cotransfected with baculovirus (Autograpa californica nuclear polyhedrosis virus) DNA into insect cells by calcium phosphate precipitation. Recombinant baculovirus in which the pAc373 polyhedrin gene containing a HRSV cDNA has replaced the resident viral polyhedrin gene by homologous recombination is detected by dot blot hybridization, Summers, M. and Smith, G., A Manual of Methods for Baculovirus Vectors and Insert Cell Culture Procedures, Texas A & M University, College Station, Tex., p. 29-30 (1986) using $^{32}P$-labeled HRSV cDNA as a probe. Insect cells infected with recombinant baculovirus may also be differentiated by their inclusion-negative morphology since the insertion of the HRSV cDNA into the polyhedrin gene prevents the synthesis of this inclusion-forming protein. Isolation of HRSV proteins from infected insect cells is accomplished as described for CHO cells.

The preferred expression vector used in conjunction with bovine papilloma virus (BPV) for expressing HRSV-like proteins is pTFW9. The plasmid replicates in *E. coli* utilizing ampicillin resistance, and provides the mouse metallothionein promoter and SV40 polyadenylation signal for expression of HRSV genes. Plasmid pTFW9 is cleaved and a HRSV cDNA is inserted adjacent to the promoter. This new plasmid is then cleaved to allow insertion of BPV. The recombinant plasmid is transfected into animal cells by calcium phosphate precipitation and foci of transformed cells are selected. HRSV protein expressed in these transformed cells is isolated as described for CHO cells.

Host cells are competent or rendered competent for transfection by various means. There are several well-known methods of introducing DNA into animal cells. These include: calcium phosphata precipitation, fusion of the recipient cells with bacterial protoplasts containing the DNA, treatment of the recipient cells with liposomes containing the DNA, and microinjection of the DNA directly into the cells.

The transfected cells are cultured by means well known in the art. Biochemical Methods in Cell Culture and Virology, Kuchler, R. J., Dowden, Hutchinson and Ross, Inc., (1977) and the expressed HRSV-like proteins analogs are isolated from cell suspensions created by disruption of the host cell system by well known mechanical or enzymatic means. HRSV-like proteins which are designed to be secreted from the cells are isolated from the media without disruption of the cells.

Isolation of the HRSV proteins is accomplished by lysing the CHO cells with detergents. For HRSV glycoproteins it is helpful to first apply the cytoplasmic fraction to a lentil lectin column which will specifically bind glycoproteins. The eluted glycoproteins are then applied to an affinity column containing anti-HRSV antibody. Non-glycoproteins of HRSV can be directly applied to the affinity column.

F. Definitions

The phrase "cell culture" refers to the containment of growing cells derived from either a multicellular plant or animal which allows for the cells to remain viable outside the original plant or animal.

The term "downstream" identifies sequences proceeding farther in the direction of expression; for example, the coding region is downstream from the initiation codon.

The term "microorganism" includes both single cellular prokaryote and eukaryote organisms such as bacteria, actinomycetes and yeast.

The term "operon" is a complete unit of gene expression and regulation, including structural genes, regulator genes and control elements in DNA recognized by regulator gene product.

The term "plasmid" refers to an autonomous self-replicating extrachromosomal circular DNA and includes both the expression and nonexpression types. Where a recombinant microorganism or cell culture is described as hosting an expression plasmid the phrase "expression plasmid" includes both extrachromosomal circular DNA and DNA that has been incorporated into the host chromosome(s). Where a plasmid is being maintained by a host cell, the plasmid is either being stably replicated by the cells during mitosis as an autonomous structure or as an incorporated portion of the host's genome.

The term "promoter" is a region of DNA involved in binding the RNA polymerase to initiate transcription.

The phrase "immunogenic fragment(s)" includes derivatives of the structural proteins of HRSV having sufficient antigenic capacity to produce effective immunologic protection in patient exposed to virulent HRSV. The phrase "HRSV-like proteins" is meant to encompass these fragments. For example, HRSV proteins are made up of amino acid residues, not all of which are exposed to the aqueous environment and capable of eliciting a strong immunogenic response. If carefully selected, modification or deletion to these regions would not affect antigenicity. While no longer being native HRSV proteins, the proteins are now immunogenic fragments if deletions are involved and HRSV-like proteins if either deletions or modifications to the primary sequence were involved.

The phrase "DNA sequence" refers to a single or double stranded DNA molecule comprised of nucleotide bases, adenosine, thymidine, cytosine and guanosine.

The phrase "essentially pure (HRSV) protein" refers to compositions of viral protein that contain no virus synthesized protein. Although the essentially pure proteins may be contaminated with low levels of host cell constituents, the protein is devoid of contaminating structural and non-structural viral protein produced by replicating HRSV.

The phrase "suitable host" refers to a cell culture or microorganism that is compatible with a recombinant plasmid and will permit the plasmid to replicate, to be incorporated into its genome or to be expressed.

The term "upstream" identifies sequences proceeding in the opposite direction from expression; for example, the bacterial promoter is upstream from the transcription unit, the initiation codon is upstream from the coding region.

Conventions used to represent plasmids and fragments in Charts 1-6, are meant to be synonymous with conventional circular representations of plasmids and their fragments. Unlike the circular figures, the single line figures on the charts represent both circular and linear double-stranded DNA with initiation or transcription occurring from left to right (5' to 3'). Asterisks (*) represent the bridging of nucleotides to complete the circular form of the plasmids. Fragments do not have asterisk marks because they are linear pieces of double-stranded DNA. Endonuclease restriction sites are indicated above the line. Gene markers are indicated below the line. Bars appearing below the diagrams representing the plasmid or fragments are used to indicate the number of basepairs between two points on the DNA. The relative spacing between markers do not indicate actual distances but are only meant to indicate their relative positions on the illustrated DNA sequence.

EXAMPLES

Example 1

The Cloning of HRSV Glycoproteins F and G

A. Virus and Cells

The $A_2$ strain of RS virus, available from the American Type Culture Collection, Bethesda, Md., is propagated in monolayer cultures of HEp-2 cells in Eagle minimum essential medium supplemented with 5% heat-inactivated fetal calf serum. Viral infectivity is measured by cytopathic effect on monolayer cultures of HEP-2 cells.

B. Preparation of Radiolabeled RS Virus Intracellular RNAs

Monolayer cultures of HEp-2 cells are infected with RS virus at a multiplicity of infection of 1 PFU per cell. After 2 hours of adsorption at 37° C., fresh Eagle minimal essential medium supplemented with 5% heat-inactivated fetal calf serum is added. At 14 hours postinfection, the cells are treated with 5 μg of actinomycin D per ml. The cells are then exposed to $[^3H]$uridine at 20 μCi/ml in the presence of drug from 16 to 20 h p.i.

C. Preparation of Purified HRSV mRNA's

At 20 hours postinfection, cells are suspended in HBS solution (10 mM N-2-hydroxyethylpiperazine-N'-2-ethanesulfonic acid, pH 7.6, 10 mM NaCl, 1 mM $MgCl_2$) and broken by Dounce homogenization. Nuclei are removed by centrifugation at 2,000×g. The supernatant is made approximately 4.5M with respect to CsCl and 1.5% in N-lauryl sarcosine and is layered over 2 ml of 5.7M CsCl solution containing HBS, 0.1M EDTA, and 2% N-lauryl sarcosine. After 12 to 24 h of centrifugation in a Beckman SW40 rotor at 25,000 rpm and 22° C., the clear RNA pellet is resuspended in sterile water, brought to 0.2M NaCl-0.2% sodium dodecyl sulfate, SDS, and ethanol precipitated. After a second precipitation with ethanol, mRNA's are isolated by binding to oligodeoxythymidylate oligo(dT)-cellulose in 0.01M tris-hydrochloride, pH 7.5, containing 0.02% SDS and 0.5M NaCl, and eluting in the above minus the NaCl. Eluted mRNA's are precipitated with ethanol after addition of rabbit liver tRNA carrier and NaCl to 0.2M.

D. cDNA Synthesis

The synthesis of cDNA follows conditions designed to maximize cDNA length, Land, H. et al. Nuc. Acids Res. 9:2251-2266 (1981). Twenty-five micrograms of poly(A)+ RNA from RS virus-infected cells is transcribed into cDNA by using 40 μg of oligo(dT) as primer and 140 units of avian myeloblastosis virus reverse transcriptase (Life Sciences, St. Petersburg, Fla.) in a 500-μl reaction mixture containing: Tris.HCl (50 mM, pH 8.3); $MgCl_2$ (10 mM); dithiothreitol (30 mM); KCl (120 mM); sodium pyrophosphate (4 mM); dTTP, dATP, and dGTP (1 mM each); $[^3H]$dCTP (ICN Radiochemicals, 0.8 mCi, 0.4 Ci/mmol; 1 Ci$=3.7\times10^{10}$ becquerels); and $(dT)_{12-18}$ (80 μg/ml); and mRNA (50 μg/ml). The mixture is incubated for 1 hr at 43° C. and the reaction is terminated by phenol-chloroform extraction and ethanol precipitation.

The nucleic acids are resuspended in water and incubated for 2 h at 37° C. in the presence of 0.3M NaOH (final volume, 300 μl). The mixture is neutralized by the additions of 25 μl of 2.5M Tris-hydrochloride (pH 7.6) and 30 μl of 2M HCl and is immediately passed through Sephadex G-200 with a column buffer of 1 mM Tris-hydrochloride (7.6). The cDNAs contained in the leading edge of the void volume are collected. Homopolymeric dCMP tails are added in a 550-μl reaction mixture containing 325 units of terminal transferase (P-L Biochemicals). The reaction mixture is incubated at 15° C. Aliquots are withdrawn after 2.5 and 5 min and adjusted to 10 mM EDTA, and the cDNAs are purified by extraction with phenol-chloroform, followed by three rounds of ethanol precipitation.

Synthesis of the second cDNA strand is performed in a 600-μl reaction mixture under the conditions described above for reverse transcription of nRNA, except the actinomycin D is omitted, the oligodeoxythymidylate is replaced by 30 μg of oligodeoxyguanylate$_{12-18}$ (P-L Biochemicals) per ml, and the reaction contains 0.75 mCi of $[\alpha\text{-}^{32}P]$dCTP (specific activity, 3,000 Ci/mmol; Amersham Corp.). After incubation for 1 h at 43° C., the reaction mixture is passed directly through Sepharose 6B, and the cDNAs in the void volume are recovered. To obtain maximum completion of second-strand synthesis, the cDNAs are placed in a 400-μl reaction mixture containing 10 mM Tris-hydrochloride (pH 7.6), 8 mM magnesium acetate, 70 mM KCl, 10 mM dithioerythritol, 0.5 mM each deoxynucleotide, and 12 units of DNA polymerase I (Klenow fragment) (P-L Biochemicals). After incubation for 2 h at 15° C., the reaction is terminated by the addition of EDTA to 10 mM. The products are purified by extraction with phenol-chloroform and passage through Sepharose 6B. Homopolymer dCMP tails are added in a 600-μl reaction mixture under the conditions described above, except incubations take place at 30° C. for 2.5 and 5 min. The reactions are terminated by the addition of EDTA and by extraction with phenol-chloroform, and the products are collected by ethanol precipitation.

E. Tailing and Annealing of the cDNA to Vector DNA

Vector DNA, prepared by digesting pBR322 to completion with Pstl and adding homopolymer tracts of dGTP residues, is commercially available from New England Nuclear. The vector NDA can also be made according to the methods described above. The procedure for annealing cDNA with vector DNA is also described by Maniatis. Briefly, tailed cDNA is mixed with vector in a 1:1 molar ratio in a 50 μl reaction containing 10 mM Tris pH 7.4; 0.4M NaCl; 1 mM EDTA. Final DNA concentrations varied between 20-60 μg/ml. Annealing is accomplished by either; 1) following a defined regimen of incubations consisting of 65°/10'; 42°/60'; 37°/2 hours, and then room temperature for 2 hours, or 2) incubation at 65°/10' shutting off the water bath and allowing it to slowly equilibrate to room temperature overnight.

The cDNA containing vectors are introduced into *E. coli* using transformation procedures already described. The bacteria are screened in situ using the hybridization procedures also described earlier.

Radioactively labeled $^{32}P$ hybridization probes are prepared by either of the following methods. The probes may be prepared by reverse transcription of infected cell mRNA which has been prehybridized with uninfected cell mRNA to remove the cellular RNA, or by reverse transcription viral RNA isolated from purified nucleocapsids. Collins, P. L. and Wertz, G., Proc. Natl. Acad. Sci. USA, 80:3208-3212 (1983). Identification of specific cDNAs are achieved by hybrid selection, cell-free translation and immunoprecipitation as described in Collins, P. L. et al., J. Virol. 49(2):572–578 (1984).

The preferred method for colony hybridizations utilizes the sequences disclosed herein to construct the pentadecamers described below as probes. For use as a hybridization probe one μg of 15-mer is phosphorylated in a 50 μl reaction volume consisting of 70 mM Trisbase (pH 7.6), 100 mM KCl; 10 mM $MgCl_2$, 5 mM dithiothreitol, 50 μCi $\gamma^{32}P$ dATP (P. L. Biochemicals), and 1 U $T_4$ polynucleotide kinase (New England Biolabs). Incubation is at 37° C. for 60 minutes. In this fashion the 15-mer can be labeled to a specific activity of $1 \times 10^8$ cpm per μg.

F. Plasmids pGPF (chart 1) and pGPG.

Clones exhibiting complementary sequences to the probes complementary to the 5′ region of the F and G glycoproteins are selected for secondary screening using Pstl restriction analysis of the clones to determine if the digestion products are consistent with the Pstl restriction map which can be obtained from the sequence given in Charts 12 to 16.

As final proof, a mini-preparation of DNA is isolated from the clone and is sequenced by dideoxy chain termination. Minipreps of plasmid DNA are prepared as described in the General Methods section. Dideoxy sequencing is carried out as described in the General Methods section using the synthetic pentadecamers, described below, as primers in a 20:1 molar excess over template.

G. Synthesizing oligonucleotides complementary to HRSV-like proteins

Oligonucleotides are chemically synthesized according to the solid phase phosphoramidite triester method first described by Beaucage S. L. and Caruthers, M. H. Tetrahedron Letts. 22(20):1859–1862 (1981) using an automated synthesizer, as described in Needham-VanDevanter, D. R., et al., Nucleic Acids Res., 12:6159–6168 (1984). Purification of oligonucleotides was by either native acrylamide gel electrophoresis or by anion-exchange HPLC as described in Pearson, J. D. and Regnier, F. E., J. Chrom., 255:137–149 (1983).

The sequence of the synthetic oligonucleotides can be verified using the chemical degradation method of Maxam, A. M. and Gilbert, W., Grossman, L. and Moldave, D., eds., Academic Press, New York, Methods in Enzymology, 65:499–560 (1980). Alternatively, the sequence can be confirmed after the assembly of the oligonucleotide fragments into the double-stranded DNA sequence using the method of Maxam and Gilbert, supra, or the chain termination method for sequencing double-stranded templates of Wallace, R. B. et al, Gene, 16:21–26 (1981).

The oligonucleotides from the 3′-end of the mRNA can be used to specifically prime the reverse transcription reaction for making the first strand of the cDNA. The oligonucleotides from the 5′-ends can be used to probe for full length cDNA specific for that gene. The following 15-mer oligonucleotides are useful for the above purposes although alternative sequences could be used.

<u>Ggp</u>
<u>5′-end</u> ATGTCCAAAAACAAG
<u>3′-end</u> ACACCACGCCAGTAG

<u>Fgp</u>
<u>5′-end</u> ATGGAGTTGCTAATC
<u>3′-end</u> GCATTTAGTAACTAA

<u>1A</u>
<u>5′-end</u> ATGGAAAATACATCC
<u>3′-end</u> CGAGTCAACACATAG

<u>Nuc</u>
<u>5′-end</u> ATGGCTGTTAGCAAA
<u>3′-end</u> GATGTAGAGCTTTGA

<u>22K</u>
<u>5′-end</u> ATGTCACGAAGGAAT
<u>5′-end</u> AATGATACTACCTGA

Oligonucleotides for Use in λ Exonuclease Step

<u>Fgp</u>
CAAATAACAATGGAG

<u>Ggp</u>
CAAACATGTCCAAAA

Example 2

Expression of Glycoproteins F (gpF) and G (gpG) of HRSV in CHO cells

The same procedures and enzymes will be used for both glycoproteins unless otherwise noted.

In order to obtain maximum expression of the F glycoprotein, the G-C nucleotides which are used to insert the cDNA into the plasmid pBR322 must be removed from the 5′ end (relative to the original mRNA) of the cDNA. In order to conveniently insert the gpF cDNA into the preferred expression vector for CHO cells, pSVCOW7 (described below), it is necessary to supply a BamHI site upstream from the protein coding sequence. To accomplish this the cDNA of F or G glycoprotein is inserted into pUC12 (PL Pharmacia Labs, Piscataway, N.J.).

A. Construction of pGPF2—Chart 2

The cDNA of the glycoproteins is flanked by PstI sites, Chart 1, however, there are also internal PstI sites. Therefore, the plasmid pGPF is partially digested with PstI and fragment 2 (1.9 kb; gpG cDNA is 0.9 kb) is isolated from a gel. Fragment 2 is ligated to the plasmid pUC12 (Bethesda Res. Labs., Rockville, Md.) which had been digested with PstI. A plasmid with the 5′ end of the gpF gene adjacent to the XbaI site in pUC12 is selected and designated pGPF2 (4.6 kb). This orientation is verified by cleavage with AccI which generates a fragment of approximately 200 bp (for gpG, orientation is verified by digestion with HincII, generating a fragment of approximately 400 bp).

B. Construction of pGPF3—Chart 3

To remove the G-C nucleotides from the 5′ end of the cDNA, pGPF2 is opened with XbaI and the ends are treated with bacterial alkaline phosphatase to yield fragment 4. Fragment 4 is then digested with SalI which cuts off a small piece between the XbaI and PstI sites and treated with Klenow enzyme to make the ends flush. After treatment with Klenow enzyme, fragment 2 is digested with Lambda exonuclease which requires a 5′ phosphate and leaves a 3′ overhand. Because of the removal of the 5′ phosphate on the end upstream from the gpF, the exonuclease will digest downstream toward the gpF sequence. The exonuclease is allowed sufficient time to remove nucleotides beyond the G/C tail region to the leader sequence. A synthetic sequence containing the first 15 bases of the leader sequence is hybridized to fragment 4 and the missing bases filled in with Klenow enzyme and the ends ligated with T4 ligase to yield pGPF3 (4.6 kb) which is transformed into *E. coli* and its sequence verified.

To remove the G-C nucleotides from the 3′ end of the cDNA, pGPF3 is opened with HindIII and treated with the exonuclease Bal 31 for a time sufficient to digest through the G-C nucleotides. The ends are made blunt with Klenow enzyme and the cDNA clone is freed from the vector DNA by digestion with BamHI. The cDNA fragment is isolated from a gel and ligated to plasmid pUC12 which has been digested with BamHI and HincII (HincII is compatible with blunt ends) to yield pGPF4. The plasmid is transformed into *E. coli* and an appropriate clone which was sufficiently digested with Bal31 is identified by sequencing. Alternatively, the G-C nucleotides may be removed by digesting with a restriction enzyme which has a unique site upstream from the G-C nucleotides. For gpF such an enzyme whould be HaeIII and for gpG FokI. These ends would by made flush and the DNA treated as described above for generating pGPF4. Since these enzymes cleave upstream from their gene's normal translation termination signal, a universal translation termination oligonucleotide (New England Biolabs) would be ligated into an appropriate enzyme site.

C. Construction of pSVCOW7—Chart 4

The starting plasmid pSV2dhfr (available from the American Type Culture Collection or prepared according to the procedure of S. Subramani, et al., "Expression of the Mouse Dihydrofolate Reductase Complementary Deoxyribonucleic Acid in Simian Virus 40", Molecular and Cellular Biology 2:854–864 (Sep. 1981) is digested with BamHI and EcoRI to yield fragment 5 (5.0 kb) containing the ampicillin resistance gene, the SV40 origin, and the dhfr gene. The second portion of pSVCOW7 is obtained from plasmid pλGH2R2 which is digested with the same restriction endonucleases used to cleave pSV2dhfr to obtain fragment 6 (2.1 kb) containing the 3′ end of genomic bovine growth hormone gene, i.e., BGH gDNA. Plasmid pλGH2R2 is publicly available from an *E. coli* HB101 host, deposited with the Northern Regional Research Laboratories in Peoria, Ill. (NRRL B-15154). Fragments 5 and 6 are ligated to yield pSVCOW7 (7.1 kb).

D. Construction of pGPF-IE-PA—Charts 5–6

The assembly of pGPF-IE-PA is accomplished in two steps. First the GpF cDNA from pGPF3 is inserted into pSVCOW7 yielding pGPF-PA and then the immediate early promoter of cytomegalovirus is inserted to initiate transcription of the HRSV-like proteins yielding pGPF-IE-PA. Cl Step 1

Plasmid pSVCOW7 is cut with EcoRI and PuvI and fragment 7 (600 bp) containing the polyadenylation sequence of bovine growth hormone extending from the PvuII site in the 3′ most exon of the BGH gene, to the EcoRI site downstream from the 3′ end is isolated. For a complete discussion of the BGH polyadenylation sequence see the following references: European Patent Application 0112012, published on 27 Jun. 1984 wherein the identification and characterization of BGH genomic DNA is disclosed; Woychik, R. P. et al., Requirement for the 3′ Flanking Region of the Bovine Growth Gene for Accurate Polyadenylation, Proc. Natl. Acad. Sci. USA 81:3944–3948 (Jul. 1984) and Higgs et al., Nature, 306:398–400 (24 Nov. 1983) and references cited therein disclosing that the nucleotide sequence AATAAA characterizes the polyadenylation signal at a location 11 to 30 nucleotides upstream from the 3′ end of the BGH gene.

A second sample of pSVCOW7 is cut with EcoRI and BamHI to yield fragment 8. Fragment 8 can be alternatively derived from the EcoRI/BamHI fragment from parent plasmid pSV2dhfr available from Bethesda Research Laboratories. Fragment 8 contains the origin of replication from pBR322 and an ampicillin resistance gene expressed in *E. coli* which allows for the selection of the plasmid in *E. coli.* The fragment also contains the mouse dihydrofolate reductase cDNA in a construction that allows expression in mammalian cells, Subramani et al., Mol. Cell. Biol., 1:854–864 (1981).

Plasmid pGPF3 is cut with HindIII, treated with Klenow enzyme and recut with BamHI to yield fragment 9 (1.9 kb) which is gel isolated. Fragment 9 contains the leader and structural coding sequences from GpF cDNA. The BamHI site is just upstream from the cDNA coding for the 5′ untranslated sequences of the mRNA, and the HindIII site is in pUC12 vector a few bases pairs beyond the PstI site near the 3′ end of the gpF cDNA.

Fragments 7, 8 and 9 are ligated to form pGPF-PA (7.3 kb) which is a replication vector capable of shuttling between *E. coli* and CHO cells. Plasmid pGPF-PA is transformed into *E. coli.*

Step 2

In step 2, pGPF-PA is converted into expression plasmid pGPF-IE-PA by inserting the immediate early gene promoter from human cytomegalovirus, Chart 6. The CMV I.E. promoter is obtained from the PstI digestion of the CMV genome. The restriction endonuclease cleavage maps of the region of the human cytomegalovirus (CMV) genome containing the major immediate early gene (CMV I.E.) have been described in detail by Stinski et al., J. Viol., 46:1–14 (1983), Stenberg et al., J. Virol., 49:190–199 (1984) and Thomsen et al., Proc. Natl. Acad. Sci. USA, 81:659–663 (1984). The Stinski and Thomsen references describe a 2.0 kilobase PstI fragment which contains the promoter for the major immediate early gene. When this 2.0 PstI fragment is isolated and digested with Sau3AI, a 760 base pair fragment is obtained among the products. This 760 base pair fragment can be distinguished from the other products by its size and the presence of a SacI cleavage site and a BalI cleavage site within the fragment. Because of its convenient identification, utilization of this Sau3AI fragment is the preferred method of use of the CMV I.E. promoter as described in the present specification.

Plasmid pGPF-PA is cleaved with BamHI, and a Sau3AI fragment containing the CMV immediate early promoter is ligated into the compatible BamHI site. Plasmids containing the CMV promoter fragment in an orientation such that transcription from the promoter would synthesize an mRNA for an HRSV-like protein are identified by cleavage of the plasmids with SacI. The resulting plasmid is designated pGPF-IE-PA having the CMV I.E. promoter at the 5=-end of the cDNA and the BGH polyadenylation signal on its 3'-end. The same procedures are used to obtain an equivalent expression vector for GpG. The plasmid is maintained in *E. coli* until transfection into CHO cells.

E. Transfection and Culturing of CHO Cells

Plasmid pGPF-IE-PA is transfected into Chinese hamster ovary (CHO) cells deficient in dihydrofolate reductase (dhfr) using the calcium phosphate method for transfection of DNA into cells which is described in detail by Graham et al., Introduction of Macromolecules into Viable Mammalian Cells, Alan R. Liss Inc., N.Y., p. 3-25 (1980). The cell line used is the mutant DXB-11 originally available from L. Chasin of Columbia University and completely described in Proc. Natl. Acad. Sci. USA 77:4216-4220 (1980). The above methods for transfection relies on the fact that cells which incorporate the transfected plasmids are no longer dhfr deficient and will grow in Dulbecco's modified Eagle's medium plus proline.

CHO cells expressing an HRSV-like protein are washed in phosphate buffered saline (PBS) at pH 7.4 and then lysed in PBS containing 1.0% Triton X-100 and 1.0% sodium deoxycholate. After pelleting the nuclei, the supernatant is applied to a conconavalin A column. The glycoproteins are eluted after extensive washing with a linear gradient of α-D-methylglucoside (0-0.5M) in the above buffer. The eluted glycoproteins are dialyzed against PBS containing 0.1% Triton X-100 and applied to an affinity column. The affinity column is composed of either polyclonal or monoclonal antibodies of HRSV linked to Sepharose 4B beads (Pharmacia, Piscataway, N.J.) by known techniques. The column is washed in dialysis buffer and the HRSV glycoproteins are eluted with PBS containing 0.1M glycine (pH 2.5) and 0.1% Triton X-100. The glycoprotein is dialyzed against saline and checked for purity by electrophoresis on a SDS-PAGE gel.

Example 3

The expression of HRSV GPF using Bovine Papilloma Virus (BPV)

A. The construction of a cloning vector containing a non-transcribable expression cassette suitable for replication in *E. coli.*

The constructions of pTFW8 and pTFW9 offer a convenient starting material for expressing HRSV proteins using BPV. The transcription terminator of the deposited plasmid prevents the expression of HRSV proteins and must be removed in a single step excision and ligation.

a. Construction of PTFW8—Chart 7

Plasmid pdBPV-MMTneo (342-12) is described in Mol. and Cell Biol., 3(No. 11):2100-2115 (1983) and is obtained from Peter Howley of the National Cancer Institute, Bethesda, Md. U.S.A. Plasmid pdBPV-MMT neo (342-12) consists of three parts: a complete BPV-1 genome (100%) opened at the unique BamHI site; pML2 (a "poison-minus" derivative of pBR322); and a transcriptional cassette composed of the murine metallothionein I gene promoter, the neomycin phosphotransferase II gene of Tn5, and the simian virus 40 early-region transcriptional processing signals. Plasmid pdBPV-MMT neo (342-12) is first digested with BamHI to remove the BPV sequences which were isolated and stored for later insertion. The remaining fragment is religated using T4 ligase to form pMMpro.nptII (6.7 kb). Removal of the BPV genome facilitates later genetic manipulations by creating unique restriction sites in the remaining plasmid. After the recombinations are complete, the BPV genome is replaced.

Plasmid pMMpro.nptII was digested with BglII and a synthetic DNA fragment 11 containing unique restriction sites is inserted and ligated using T4 ligase to yield pTFW8 (6.7 kb). Plasmid pTFW8 is identical to pMMpro.nptII except for the insertion of unique restriction sites between the murine metallothionein I gene promoter and the neomycin resistance gene.

b. Construction of pTWF9—Chart 8

Plasmid pTWF9 contains the transcription terminator $T_I$ from phage lambda inserted between the metallothionein I gene promoter and the neomycin resistance gene. The transcription terminator can be obtained from Donald Court of the National Cancer Institute in Bethesda, Md. U.S.A. The transcription terminator is supplied in pKG1800sib3 which is the same as pUS6 as described in Gene, 28:343-350 (1984), except that $t_I$ carries the sib3 mutation as described by Guarneros et al., PNAS, 79:238-242 (1982). During the normal infection process of phage lambda, the $t_I$ terminator functions in the inhibition of bacteriophage λ int gene expression from $P_L$ and in the termination of int gene transcription originating from $P_I$. The terminator is excised from pKG1800sib3 using AluI and PvuI as fragment 12 (1.2 kb), which is gel isolated and XhoI linkers are placed on either end of the fragment. The liners are available from New England Biolabs, Beverly, Mass. U.S.A. The terminator fragment bounded by XhoI complementary ends is then inserted into pTWF8 which has been previously digested with XhoI. The fragments are then ligated using T4 DNA ligase to yield pTWF9 (7.9 kb). Plasmid pTWF9 was desposted in accordance with the Budapest Treaty. Plasmid pTFW9 is maintained in an *E. coli* host and has been deposited with the Northern Regional Research Center, Peoria, Ill., U.S.A. on Nov. 17, 1986 and assigned Accession Number NRRL B-18141.

B. The construction of pTFW/GPF—Chart 9

In this example secretion of the glycoprotein into the culture media is desired. Therefore a universal translation termination oligonucleotide is ligated into the NsiI restriction enzyme site of the gpF gene in pGPF4 to cause a truncated glycoprotein which is missing its "anchor region" as described earlier. The modified plasmid is designated pGPF5. To construct pTFW/GPF, pGPF5 is digested with BamHI and Hind III. Its ends are made flush with Klenow enzyme and synthetic BglII linkers (New England Biolabs) are ligated to the ends of the clone. The DNA is digested with BglII and designated fragment 13 (1.9 kb). Fragment 13 containing the gpF gene is then isolated from a gel. The purified fragment is ligated into pTFW9 which has been digested with BglIII to yield pTFW/GPF (9.8 kb).

C. Conversion of pTFW/GPF into a eukaryote expression vector—Chart 10

Plasmid pTFW/GPF is converted into a eukaryote expression vector by reinserting the 100% complete BPV-1 genome excised with BamHI in step a., of Example 2. A. Plasmid pTFW/GPF is cut with BamHI and the BPV-1 intact genome, a 7.9 kb fragment (Chart 7), is inserted to yield pTFW/GPF/BPV* (17.7 kb) which is replicated in *E. coli* until production of glycoprotein F by eukaryotic cells is desired.

D. Expression of gpF in murine C127 cells

Prior to transfection into murine C127 cells, pTFW/GPF/BPV* is digested with XhoI to excise the $T_l$ terminator and religated with T4 DNA ligase. The resulting plasmid pTFW/GPF/BPV (16.5 kb) will now direct the expression of high levels of gpF which is secreted into the culture media. The C127 cells are available from the American Type Culture Collection and grown in Dulbecco's modified minimal essential media containing 10% fetal calf serum. The levels of gpF proteins in the media of the C127 cells are determined by Western blot experiments with anti-RSV antibody and $^{125}I$ labeled protein A.

HRSV gpF truncated is purified by collecting the culture media surrounding the expressing cells. Serum-free media is preferred at this point if the levels of expression are acceptable in this media. The media is clarified by low speed centrifugation and concentrated by filtration. HRSV gpF is then purified by column chromatography as described for glycoproteins produced in CHO cells.

Example 4

The Expression of HRSV GPF Using Baculovirus Virus

The following example relates to the expression of glycoprotein F in insect cell cultures. All procedures are detailed in Summers, M. D. and Smith, G. E., A Manual for Baculovirus Vectors and Insect Cell Culture Procedures published by the College of Agriculture, Texas Agricultural Experiment Station, Texas Agricultural Extension Service, College Station, Tex. (1986). The starting plasmid pAc373 (7.1 kb) is a general baculovirus expression vector having a unique BamHI site immediately downstream from the polyhedron promoter for Autographa californica nuclear polyhedrosis virus (AcNPV). The polyhedron protein is a matrix protein that is nonessential for viral infection and replication in vitro. The plasmid is available from Professor Max Summers of the Department of Entomology, Texas A & M University, College Station, Tex. 77843 and is fully described in Molecular and Cell. Biology, 3(12):2156–2165 (1983).

A. Construction of pAcGPF—Chart 11

Plasmid pGPF5 is digested with HindIII and the ends are made flush with Klenow enzyme. Synthetic BamHI linkers (New England Biolabs) are ligated to the end of the DNA. The DNA is digested with BamHI and fragment 14 containing the gpF gene is isolated from a gel. The purified fragment is ligated into pAc373 which has been digested with BamHI.

B. Transfection and Culturing of *S. frugiperda*

The gpF cDNA insert of pAcGPF is recombined with native AcNPV DNA by cotransfection in *S. frugiperda. S. frugiperda* (SF9; ATCC CRL 1711) are cultured in Grace Media (Gibco Lab. Livonia, Mich. 48150), 10% fetal calf serum and supplemented with Difco Lactalbumin hydrolysolate and yestolate. The cells are cotransfected with AcNPV DNA and pAcGPF at 1μ/ml and 2μ/ml respectively. Resulting virus particles are obtained by collecting the media and removing cellular material by low speed centrifugation. The virus containing-media is then used to infect *S. frugiperda.* Subsequent infection of *S. frugiperda* using these viral particles which include both native viral DNA and DNA recombined with the cDNA coding for glycoprotein F will result in some cells expressing the HRSV protein instead of the polyhedron protein. Purification of recombinant virus is accomplished by a series of limited dilution platings in 96-well tissue culture plates containing *S. frugiperda* cells. Wells containing recombinant virus are deleted by dot blot hybridization using pGPF4 which has been labeled with $^{32}P$-dCTP by nick translation as a probe. Once sufficiently pure, the recombinant virus is detected by its unique inclusion-negative plaque morphology. HRSV protein synthesized in recombinant baculovirus infected cells is detected by Western blot experiments with anti-RSV antibody and $^{125}I$ labeled protein A (Amersham Corp.).

The HRSV protein is purified from the culture media by the methodology described in the BPV expression system for C125 cells.

Example 5

Preparation of a Vaccine for HRSV

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents such as aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid X, Corynebacterium parvum, Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.).

The proportion of immunogen and adjuvant can be varied over a broad range so long as both are present in effective amounts. For example, aluminum hydroxide can be present in an amount of about 0.5% of the vaccine mixture. On a per dose basis, the concentration of the immunogen can range from about 0.015 μg to about 1.5 mg per kilogram per patient body weight. A preferable dosage range is from about 1.5 μg/kg to about 0.043 mg/kg of patient body weight. A suitable dose size in humans is about 0.1–1 ml, preferably about 0.1 ml. Accordingly, a dose for intramuscular injection, for example, would comprise 0.1 ml containing immunogen in admixture with 0.5% aluminum hydroxide.

The vaccine can be administered to pregnant women or to women of child-bearing age to stimulate material HRSV antibodies. The female can be revaccinated as needed. Infants can be vaccinated at 2 to 3 months of age and revaccinated as necessary, preferably at 6 to 9 months of age. Babies born to unvaccinated mothers can be vaccinated at 2 to 3 months of age. The vaccine may also be useful in other susceptible populations such as elderly or infirmed patients.

The vaccine may also be combined with other vaccines for other diseases to produce multivalent vaccines. It may also be combined with other medicaments such as antibiotics.

CHART 1. CONSTRUCTION OF pGPF (a) Plasmid pBR322 is cut with PstI and tailed with guanosine to yield fragment 1 which is gel isolated.

FRAGMENT 1

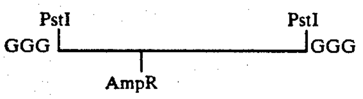

(b) cDNA from mRNA of HRSV is tailed with 10-15 dCMP residues per 3' end.

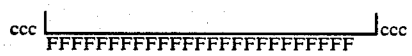

(c) Fragment 1 and the cDNA from HRSV mRNA are ligated and pGPF identified by hybridization with the appropriate probe.

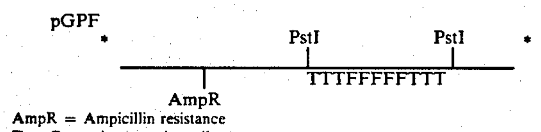

AmpR = Ampicillin resistance
T = Guanosine/cytosine tail.
F = Glycoprotein F.

CHART 2. CONSTRUCTION OF pGPF2

(a) Plasmid pGPF is cut with PstI and fragment 2 (1.9 kb) is gel isolated.

FRAGMENT 2

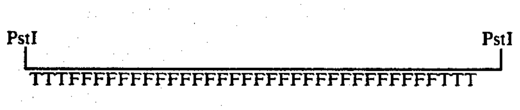

(b) Plasmid pUC12 (2.7 kb) is cut with PstI to yield fragment 3 which is gel isolated.

FRAGMENT 3

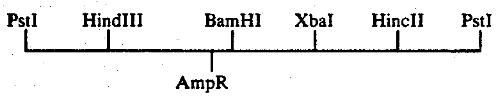

(c) Fragments 4 and 5 are ligated to yield pGPF2 (4.6 kb) which is transformed in *E. coli.*

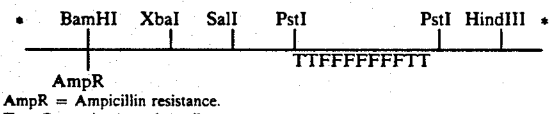

AmpR = Ampicillin resistance.
T = Guanosine/cytosine tail.
F = Glycoprotein F.

CHART 3. CONSTRUCTION OF pGPF3 and pGPF4

(a) Plasmid pGPF2 is cut with XbaI, treated with bacterial alkaline phosphatase, recut with SalI and treated with Klenow enzyme to yield fragment 4.

FRAGMENT 4

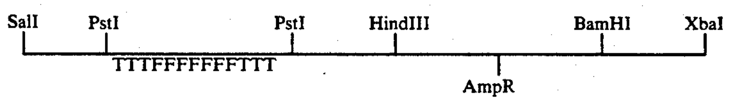

(b) Fragment 4 is digested downstream from the SalI site using lambda exonuclease and the remaining 3' tail is hybridized to the synthetic oligonucleotide complementary to the 5' portion of the leader sequence having the following sequence of GpF cDNA.

5'-end ATGGAGTTGCTAATC (c) The single stranded portion of the cDNA 3' downstream from the synthetic oligonucleotides are filled in using Klenow enzyme and the ends are ligated using T4 ligase to yield pGPF3 (4.6 kb).

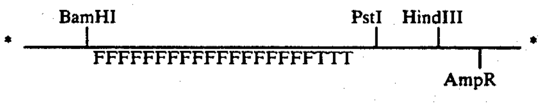

(d) Plasmid pGPF3 is cut with HindIII and treated with Bal 31 to digest the G-C nucleotide tail at the 3' end of the gpF CDNA. The gpF cDNA is cut with BamHI (1.7 kb) isolated from a gel and religated into a BamHI/HincII digestion of PUC12 to yield pGPF4 (4.4 kb).

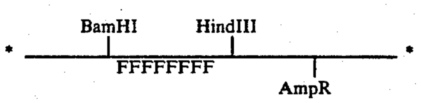

AmpR = Ampicillin resistance.
T = Guanosine/cytosine tail.
F = Glycoprotein F.

CHART 4. CONSTRUCTION OF pSVCOW7

(a) Plasmid pSV2dhfr is cut with BamHI and EcoRI to obtain fragment 5 (5.0 kb).

FRAGMENT 5

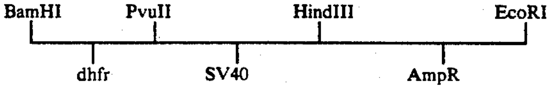

(b) Plasmid pγGH2R2 is cut with BamHI and EcoRI to obtain fragment 6 (2.1 kb).

FRAGMENT 6

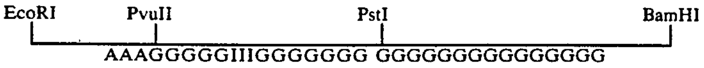

(c) Fragments 5 and 6 are ligated to yield pSVCOW7 (7.1 kb).

pSVCOW7

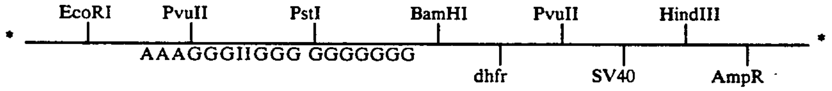

A = Bovine growth hormone poly A tail.
G = Genomic bovine growth hormone.
I = Intron.
dhfr = Dihydrofolate reductase.
SV40 = SV40 promoter and origin of replication.
AmpR = Ampicillin resistance CHART 5. CONSTRUCTION OF pGPF-PA (a) pSVCOW7 is cut with EcoRI and PvuII to yield fragment 7 (600 bp) containing the polyadenylation sequence of bovine growth hormone which is gel isolated.

FRAGMENT 7

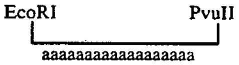

(b) pSVCOW7 is cut with EcoRI and BamHI to yield fragment 8 (5.8 kb).

FRAGMENT 8

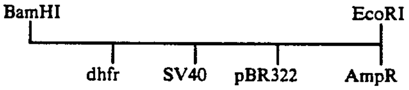

(c) Plasmid pGPF4 is cut with HindIII, treated with Klenow enzyme, cut with BamHI to yield fragment 9 (1.9 kb) containing GPF having a 3′ BamHI overhang upstream and a blunt end downstream from the message.

FRAGMENT 9

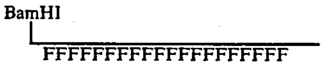

(d) Fragments 7, 8 and 9 are ligated to form pGPF-PA which is maintained in *E. coli*

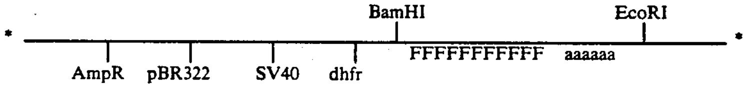

AmpR = Ampicillin resistance.
pBR322 = Replication origin for pBR322
SV40 = Replication origin for SV40
dhfr = dihydrofolate reductase
F = Glycoprotein F.
CMV = Cytomegalovirus promoter.
a = Polyadenylation tail.
T = guanosine/cytosine tail CHART 6. CONSTRUCTION OF pGPF-IE-PA (a) Plasmid pGPF-PA is cut with BamHI to yield fragment 10 (7.3 kb).

(b) The CMV immediate early promoter is obtained from a Sau3AI digestion of a PstI fragment from the CMV genome. Sau3A is compatible with BamHI for ligation.

(c) Fragment 10 and the CMV promoter are ligated to yield pGPF-IE-PA (8.0 kb).

pGPF-IE-PA

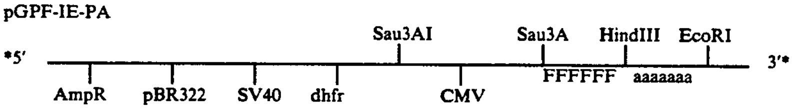

AmpR = Ampicillin resistance.
pBR322 = Replication origin for pBR322
SV40 = Replication origin for SV40
dhfr = dihydrofolate reductase
F = Glycoprotein F.
CMV = Cytomegalovirus promoter.
a = Polyadenylation tail.

CHART 7. Construction of pTFW8 a) Plasmid pdBPV-MMTneo (342-12) (14.6 kb) was cut with BamHI and the bovine papilloma virus genome was excised (7.9 kb) gel isolated and saved. The remaining fragment was gel isolated, religated using T4 ligase and designated pMMpro.nptII (6.7 kb).

pdBPV-MMTneo (342-12)

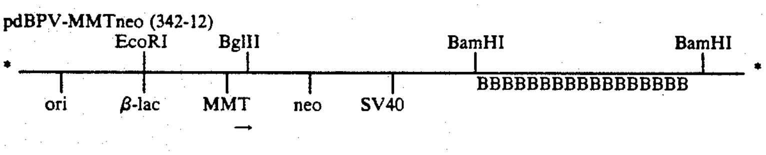

pMMpro.nptII

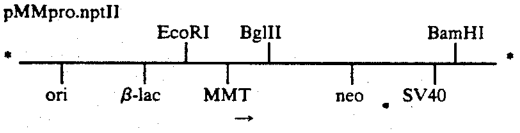

b) Plasmid pMMpro.nptII was cut with BglII and synthetic fragment 11 inserted and the plasmid religated to yield pTFW8 (6.7 kb).

Synthetic Fragment 11

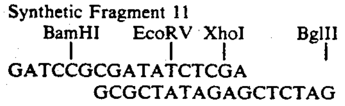

pTFW8

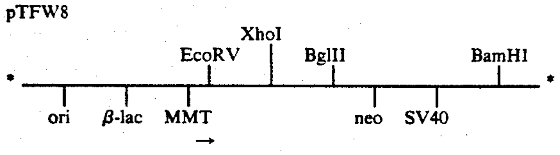

B = Bovine papilloma virus sequences.
SV40 = Simian virus 40 sequences early region, small t antigen splicing signals and 3' transcriptional processing signals.
neo = Neomycin phosphotransferase II gene (NPTII).
MMT = Murine metallothionein gene promoter.
ori = pBR322 origin of replication.
β-Lac = β-lactamase gene.

CHART 8. Construction of pTFW9 a) Plasmid pTFW8 (Chart 1) is cut with XhoI and fragment 12 containing the $t_I$ terminator from pKG1800sib3 is inserted using T4 ligase to obtain plasmid pTFW9 (7.9 kb).

FRAGMENT 12

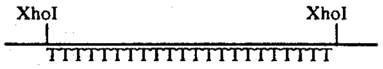

pTFW9

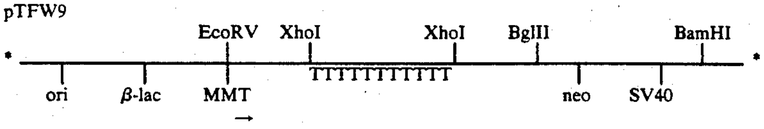

SV40 = Simian virus 40 sequences early region, small t antigen splicing signals and 3' transcriptional processing signals.
neo = Neomycin phosphotransferase II gene (NPTII).
MMT = Murine metallothionein gene promoter.
ori = pBR322 origin of replication.
β-Lac = β-lactamase gene.
T = $\lambda t_I$ terminator.

CHART 9. Construction of pTFW/GPF a) pGPF4 (Chart 3) is cut with NsiI and a translation terminator ligated into the CDNA of gpF yielding pGPF5 (4.6 kb).

pGPF5

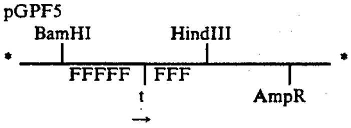

b) Plasmid pGPF5 is cut with BamHI and HindIII isolating Fragment 13 consisting of the cDNA encoding gpF (1.9 kb). The ends of fragment 13 are made blunt with Klenow enzyme and synthetic BglII linkers are ligated to the ends of the clone and the cDNA treated with BglII to yield Fragment 13.

FRAGMENT 13

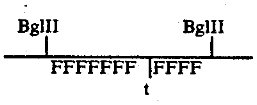

c) Plasmid pTFW9 is cut with BglII and Fragment 13 is inserted and religated to form pTFW/GPF (9.8 kb).

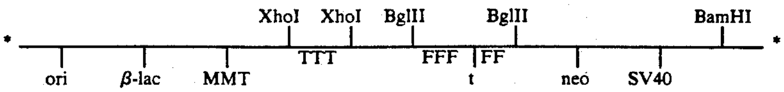

-continued

SV40 = Simian virus 40 sequences early region, small t antigen splicing signals and 3' transcriptional processing signals.
neo = Neomycin phosphotransferase II gene (NPTII).
MMT = Murine metallothionein gene promoter.
ori = pBR322 origin of replication.
β-Lac = β-lactamase gene
F = glycoprotein F
t = translation terminator.
AmpR = Ampicillin resistance.

CHART 10. Construction of pTFW/GPF/BPV a) Plasmid pTFW/GPF (Chart 9) is cut with BamHI and the intact BPV genome (from chart 7 step a) is inserted and ligated into pTFW/GPF to yield pTFW/GPF/BPV* (17.9 kb).

pTFW/GPF/BPV*

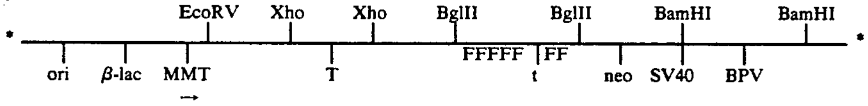

b) pTFW9/GPF/BPV* is cut with XhoI and the large fragment is religated to yield pTFW/GPF/BPV (9.3 kb).

pTFW/GPF/BPV

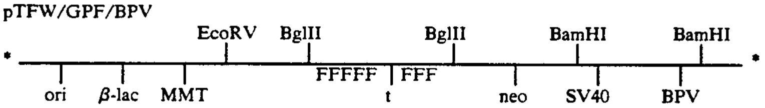

SV40 = Simian virus 40 sequences early region, small t antigen splicing signals and 3' transcriptional processing signals.
neo = Neomycin phosphotransferase II gene (NPTII).
MMT = Murine metallothionein gene promoter.
ori = pBR322 origin of replication.
β-Lac = β-lactamase gene
F = gpF protein
t = translation terminator.
T = $\lambda t_f$ terminator.

CHART 11. Construction of pAcGPF a) Plasmid pGPF5 (chart 9) is cut with HindIII and the ends made flush with Klenow enzyme. Synthetic BamHI linkers are ligated and the plasmid digested with BamHI to yield fragment 14 (1.9 kb) containing the gpF cDNA. Fragment 14 is gel isolated.

FRAGMENT 14

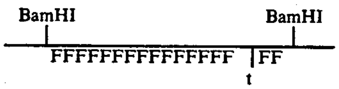

b) pAc373 (7.1 kb) is treated with BamHI to linearize pAc373 (7.1 kb).

pAc373

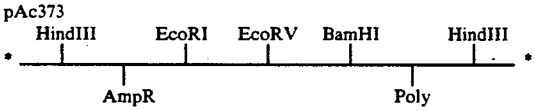

c) The linear pAc373 and fragment 14 are annealed and ligated to form pAcGPF (9.0 kb).

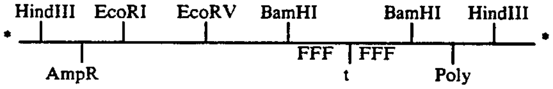

N = Untranslated 3' portion of TPAcDNA.
AmpR = Ampicillin resistance.
Poly = Polyhedrin protein gene.
F = glycoprotein F.
t = translation terminator.

CHART 12

Nucleotide sequence of the F mRNA
and the predicted protein sequence

| | | | | | | | | | | | | | | | | | | |
|---|---|---|---|---|---|---|---|---|---|---|---|---|---|---|---|---|---|---|
| | | | | | | G | GGG | CAA | ATA | ACA | ATG | GAG | TTG | CTA | ATC | CTC | AAA | 34 |
| | | | | | | | | | | | Met | Glu | Leu | Leu | Ile | Leu | Lys | 7 |
| GCA | AAT | GCA | ATT | ACC | ACA | ATC | CTC | ACT | GCA | GTC | ACA | TTT | TGT | TTT | GCT | TCT | GGT | 88 |
| Ala | Asn | Ala | Ile | Thr | Thr | Ile | Leu | Thr | Ala | Val | Thr | Phe | Cys | Phe | Ala | Ser | Gly | 25 |
| CAA | AAC | ATC | ACT | GAA | GAA | TTT | TAT | CAA | TCA | ACA | TGC | AGT | GCA | GTT | AGC | AAA | GGC | 142 |
| Gln | Asn | Ile | Thr | Glu | Glu | Phe | Tyr | Gln | Ser | Thr | Cys | Ser | Ala | Val | Ser | Lys | Gly | 43 |
| TAT | CTT | AGT | GCT | CTG | AGA | ACT | GGT | TGG | TAT | ACC | AGT | GTT | ATA | ACT | ATA | GAA | TTA | 196 |
| Tyr | Leu | Ser | Ala | Leu | Arg | Thr | Gly | Trp | Tyr | Thr | Ser | Val | Ile | Thr | Ile | Glu | Leu | 61 |
| AGT | AAT | ATC | AAG | GAA | AAT | AAG | TGT | AAT | GGA | ACA | GAT | GCT | AAG | GTA | AAA | TTG | ATA | 250 |
| Ser | Asn | Ile | Lys | Glu | Asn | Lys | Cys | Asn | Gly | Thr | Asp | Ala | Lys | Val | Lys | Leu | Ile | 79 |
| AAA | CAA | GAA | TTA | GAT | AAA | TAT | AAA | AAT | GCT | GTA | ACA | GAA | TTG | CAG | TTG | CTC | ATG | 304 |
| Lys | Gln | Glu | Leu | Asp | Lys | Tyr | Lys | Asn | Ala | Val | Thr | Glu | Leu | Gln | Leu | Leu | Met | 97 |
| CAA | AGC | ACA | CCA | CCA | ACA | AAC | AAT | CGA | GCC | AGA | AGA | GAA | CTA | CCA | AGG | TTT | ATG | 358 |
| Gln | Ser | Thr | Pro | Pro | Thr | Asn | Asn | Arg | Ala | Arg | Arg | Glu | Leu | Pro | Arg | Phe | Met | 115 |
| AAT | TAT | ACA | CTC | AAC | AAT | GCC | AAA | AAA | ACC | AAT | GTA | ACA | TTA | AGC | AAG | AAA | AGG | 412 |
| Asn | Tyr | Thr | Leu | Asn | Asn | Ala | Lys | Lys | Thr | Asn | Val | Thr | Leu | Ser | Lys | Lys | Arg | 133 |
| AAA | AGA | AGA | TTT | CTT | GGT | TTT | TTG | TTA | GGT | GTT | GGA | TCT | GCA | ATC | GCC | AGT | GGC | 466 |
| Lys | Arg | Arg | Phe | Leu | Gly | Phe | Leu | Leu | Gly | Val | Gly | Ser | Ala | Ile | Ala | Ser | Gly | 151 |
| GTT | GCT | GTA | TCT | AAG | GTC | CTG | CAC | CTA | GAA | GGG | GAA | GTG | AAC | AAG | ATC | AAA | AGT | 520 |
| Val | Ala | Val | Ser | Lys | Val | Leu | His | Leu | Glu | Gly | Glu | Val | Asn | Lys | Ile | Lys | Ser | 169 |
| GCT | CTA | CTA | TCC | ACA | AAC | AAG | GCT | GTA | GTC | AGC | TTA | TCA | AAT | GGA | GTT | AGT | GTC | 574 |
| Ala | Leu | Leu | Ser | Thr | Asn | Lys | Ala | Val | Val | Ser | Leu | Ser | Asn | Gly | Val | Ser | Val | 187 |
| TTA | ACC | AGC | AAA | GTG | TTA | GAC | CTC | AAA | AAC | TAT | ATA | GAT | AAA | CAA | TTG | TTA | CCT | 628 |
| Leu | Thr | Ser | Lys | Val | Leu | Asp | Leu | Lys | Asn | Tyr | Ile | Asp | Lys | Gln | Leu | Leu | Pro | 205 |
| ATT | GTG | AAC | AAG | CAA | AGC | TGC | AGC | ATA | TCA | AAT | ATA | GAA | ACT | GTG | ATA | GAG | TTC | 682 |
| Ile | Val | Asn | Lys | Gln | Ser | Cys | Ser | Ile | Ser | Asn | Ile | Glu | Thr | Val | Ile | Glu | Phe | 223 |
| CAA | CAA | AAG | AAC | AAC | AGA | CTA | CTA | GAG | ATT | ACC | AGG | GAA | TTT | AGT | GTT | AAT | GCA | 736 |
| Gln | Gln | Lys | Asn | Asn | Arg | Leu | Leu | Glu | Ile | Thr | Arg | Glu | Phe | Ser | Val | Asn | Ala | 241 |
| GGT | GTA | ACT | ACA | CCT | GTA | AGC | ACT | TAC | ATG | TTA | ACT | AAT | AGT | GAA | TTA | TTG | TCA | 790 |
| Gly | Val | Thr | Thr | Pro | Val | Ser | Thr | Tyr | Met | Leu | Thr | Asn | Ser | Glu | Leu | Leu | Ser | 259 |
| TTA | ATC | AAT | GAT | ATG | CCT | ATA | ACA | AAT | GAT | CAG | AAA | AAG | TTA | ATG | TCC | AAC | AAT | 844 |
| Leu | Ile | Asn | Asp | Met | Pro | Ile | Thr | Asn | Asp | Gln | Lys | Lys | Leu | Met | Ser | Asn | Asn | 277 |
| GTT | CAA | ATA | GTT | AGA | CAG | CAA | AGT | TAC | TCT | ATC | ATG | TCC | ATA | ATA | AAA | GAG | GAA | 898 |
| Val | Gln | Ile | Val | Arg | Gln | Gln | Ser | Tyr | Ser | Ile | Met | Ser | Ile | Ile | Lys | Glu | Glu | 295 |
| GTC | TTA | GCA | TAT | GTA | GTA | CAA | TTA | CCA | CTA | TAT | GGT | GTT | ATA | GAT | ACA | CCC | TGT | 952 |
| Val | Leu | Ala | Tyr | Val | Val | Gln | Leu | Pro | Leu | Tyr | Gly | Val | Ile | Asp | Thr | Pro | Cys | 313 |
| TGG | AAA | CTA | CAC | ACA | TCC | CCT | CTA | TGT | ACA | ACC | AAC | ACA | AAA | GAA | GGG | TCC | AAC | 1006 |
| Trp | Lys | Leu | His | Thr | Ser | Pro | Leu | Cys | Thr | Thr | Asn | Thr | Lys | Glu | Gly | Ser | Asn | 331 |
| ATC | TGT | TTA | ACA | AGA | ACT | GAC | AGA | GGA | TGG | TAC | TGT | GAC | AAT | GCA | GGA | TCA | GTA | 1060 |
| Ile | Cyc | Leu | Thr | Arg | Thr | Asp | Arg | Gly | Trp | Tyr | Cys | Asp | Asn | Ala | Gly | Ser | Val | 349 |
| TCT | TTC | TTC | CCA | CAA | GCT | GAA | ACA | TGT | AAA | GTT | CAA | TCA | AAT | CGA | GTA | TTT | TGT | 1114 |
| Ser | Phe | Phe | Pro | Gln | Ala | Glu | Thr | Cys | Lys | Val | Gln | Ser | Asn | Arg | Val | Phe | Cys | 367 |
| GAC | ACA | ATG | AAC | AGT | TTA | ACA | TTA | CCA | AGT | GAA | ATA | AAT | CTC | TGC | AAT | GTT | GAC | 1168 |
| Asp | Thr | Met | Asn | Ser | Leu | Thr | Leu | Pro | Ser | Glu | Ile | Asn | Leu | Cys | Asn | Val | Asp | 385 |
| ATA | TTC | AAC | CCC | AAA | TAT | GAT | TGT | AAA | ATT | ATG | ACT | TCA | AAA | ACA | GAT | GTA | AGC | 1222 |
| Ile | Phe | Asn | Pro | Lys | Tyr | Asp | Cys | Lys | Ile | Met | Thr | Ser | Lys | Thr | Asp | Val | Ser | 403 |
| AGC | TCC | GTT | ATC | ACA | TCT | CTA | GGA | GCC | ATT | GTG | TCA | TGC | TAT | GGC | AAA | ACT | AAA | 1276 |
| Ser | Ser | Val | Ile | Thr | Ser | Leu | Gly | Ala | Ile | Val | Ser | Cys | Tyr | Gly | Lys | Thr | Lys | 421 |
| TGT | ACA | GCA | TCC | AAT | AAA | AAT | CGT | GGA | ATC | ATA | AAG | ACA | TTT | TCT | AAC | GGG | TGC | 1330 |
| Cys | Thr | Ala | Ser | Asn | Lys | Asn | Arg | Gly | Ile | Ile | Lys | Thr | Phe | Ser | Asn | Gly | Cys | 439 |
| GAT | TAT | GTA | TCA | AAT | AAA | GGG | ATG | GAC | ACT | GTG | TCT | GTA | GGT | AAC | ACA | TTA | TAT | 1384 |

-continued

Nucleotide sequence of the F mRNA
and the predicted protein sequence

| | | | | | | | | | | | | | | | | | | |
|---|---|---|---|---|---|---|---|---|---|---|---|---|---|---|---|---|---|---|
| Asp | Tyr | Val | Ser | Asn | Lys | Gly | Met | Asp | Thr | Val | Ser | Val | Gly | Asn | Thr | Leu | Tyr | 457 |
| TAT | GTA | AAT | AAG | CAA | GAA | GGT | AAA | AGT | CTC | TAT | GTA | AAA | GGT | GAA | CCA | ATA | ATA | 1438 |
| Tyr | Val | Asn | Lys | Gln | Glu | Gly | Lys | Ser | Leu | Tyr | Val | Lys | Gly | Glu | Pro | Ile | Ile | 475 |
| AAT | TTC | TAT | GAC | CCA | TTA | GTA | TTC | CCC | TCT | GAT | GAA | TTT | GAT | GCA | TCA | ATA | TCT | 1492 |
| Asn | Phe | Tyr | Asp | Pro | Leu | Val | Phe | Pro | Ser | Asp | Glu | Phe | Asp | Ala | Ser | Ile | Ser | 493 |
| CAA | GTC | AAC | GAG | AAG | ATT | AAC | CAG | AGC | CTA | GCA | TTT | ATT | CGT | AAA | TCC | GAT | GAA | 1546 |
| Gln | Val | Asn | Glu | Lys | Ile | Asn | Gln | Ser | Leu | Ala | Phe | Ile | Arg | Lys | Ser | Asp | Glu | 511 |
| TTA | TTA | CAT | AAT | GTA | AAT | GCT | GGT | AAA | TCC | ACC | ACA | AAT | ATC | ATG | ATA | ACT | ACT | 1600 |
| Leu | Leu | His | Asn | Val | Asn | Ala | Gly | Lys | Ser | Thr | Thr | Asn | Ile | Met | Ile | Thr | Thr | 529 |
| ATA | ATT | ATA | GTG | ATT | ATA | GTA | ATA | TTG | TTA | TCA | TTA | ATT | GCT | GTT | GGA | CTG | CTC | 1654 |
| Ile | Ile | Ile | Val | Ile | Ile | Val | Ile | Leu | Leu | Ser | Leu | Ile | Ala | Val | Gly | Leu | Leu | 547 |
| TTA | TAC | TGT | AAG | GCC | AGA | AGC | ACA | CCA | GTC | ACA | CTA | AGC | AAA | GAT | CAA | CTG | AGT | 1708 |
| Leu | Tyr | Cys | Lys | Ala | Arg | Ser | Thr | Pro | Val | Thr | Leu | Ser | Lys | Asp | Gln | Leu | Ser | 565 |
| GGT | ATA | AAT | AAT | ATT | GCA | TTT | AGT | AAC | TAA | ATA • | AAA | ATA | GCA | CCT | AAT | CAT | GTT | 1762 |
| Gly | Ile | Asn | Asn | Ile | Ala | Phe | Ser | Asn | | | | | | | | | | 574 |
| CTT | ACA | ATG | GTT | TAC | TAT | CTG | CTC | ATA | GAC | AAC | CCA | TCT | GTC | ATT | GGA | TTT | TCT | 1816 |
| TAA | AAT | CTG | AAC | TTC | ATC | GAA | ACT | CTC | ATC | TAT | AAA | CCA | TCT | CAC | TTA | CAC | TAT | 1870 |
| TTA | AGT | AGA | TTC | CTA | GTT | TAT | AGT | TAT | AT | | | | | | | | | 1879 |

CHART 13

Nucleotide sequence of the RS virus G mRNA and the predicted protein sequence

| | | | | | | | | | | | |
|---|---|---|---|---|---|---|---|---|---|---|---|
| GGG | GCA | AAT | GCA | AAC | ATG | TCC | AAA | AAC | AAG | GAC | CAA |
| | | | | | Met | Ser | Lys | Asn | Lys | Asp | Gln |
| GAA | AGG | ACC | TGG | GAC | ACT | CTC | AAT | CAT | TTA | TTA | TTC |
| Glu | Arg | Thr | Trp | Asp | Thr | Leu | Asn | His | Leu | Leu | Phe |
| AAG | TTA | AAT | CTT | AAA | TCT | GTA | GCA | CAA | ATC | ACA | TTA |
| Lys | Leu | Asn | Leu | Lys | Ser | Val | Ala | Gln | Ile | Thr | Leu |
| ATC | TCA | ACT | TCA | CTT | ATA | ATT | GCA | GCC | ATC | ATA | TTC |
| Ile | Ser | Thr | Ser | Leu | Ile | Ile | Ala | Ala | Ile | Ile | Phe |
| AAA | GTC | ACA | CCA | ACA | ACT | GCA | ATC | ATA | CAA | GAT | GCA |
| Lys | Val | Thr | Pro | Thr | Thr | Ala | Ile | Ile | Gln | Asp | Ala |
| ACA | ACC | CCA | ACA | TAC | CTC | ACC | CAG | AAT | CCT | CAG | CTT |
| Thr | Thr | Pro | Thr | Tyr | Leu | Thr | Gln | Asn | Pro | Gln | Leu |
| CCG | TCT | GAA | ATT | ACA | TCA | CAA | ATC | ACC | ACC | ATA | CTA |
| Pro | Ser | Glu | Ile | Thr | Ser | Gln | Ile | Thr | Thr | Ile | Leu |
| GTC | AAG | TCA | ACC | CTG | CAA | TCC | ACA | ACA | GTC | AAG | ACC |
| Val | Lys | Ser | Thr | Leu | Gln | Ser | Thr | Thr | Val | Lys | Thr |
| CAA | ACA | CAA | CCC | AGC | AAG | CCC | ACC | ACA | AAA | CAA | CGC |
| Gln | Thr | Gln | Pro | Ser | Lys | Pro | Thr | Thr | Lys | Gln | Arg |
| AAA | CCC | AAT | AAT | GAT | TTT | CAC | TTT | GAA | GTG | TTC | AAC |
| Lys | Pro | Asn | Asn | Asp | Phe | His | Phe | Glu | Val | Phe | Asn |
| TGC | AGC | AAC | AAT | CCA | ACC | TGC | TGG | GCT | ATC | TGC | AAA |
| Cys | Ser | Asn | Asn | Pro | Thr | Cys | Trp | Ala | Ile | Cys | Lys |
| CCA | GGA | AAG | AAA | ACC | ACT | ACC | AAG | CCC | ACA | AAA | AAA |
| Pro | Gly | Lys | Lys | Thr | Thr | Thr | Lys | Pro | Thr | Lys | Lys |
| AAA | AAA | GAT | CCC | AAA | CCT | CAA | ACC | ACT | AAA | TCA | AAG |
| Lys | Lys | Asp | Pro | Lys | Pro | Gln | Thr | Thr | Lys | Ser | Lys |
| CCC | ACA | GAA | GAG | CCA | ACC | ATC | AAC | ACC | ACC | AAA | ACA |
| Pro | Thr | Glu | Glu | Pro | Thr | Ile | Asn | Thr | Thr | Lys | Thr |
| CTC | ACC | TCC | AAC | ACC | ACA | GGA | AAT | CCA | GAA | CTC | ACA |
| Leu | Thr | Ser | Asn | Thr | Thr | Gly | Asn | Pro | Glu | Leu | Thr |
| CAC | TCA | ACT | TCC | TCC | GAA | GGC | AAT | CCA | AGC | CCT | TCT |
| His | Ser | Thr | Ser | Ser | Glu | Gly | Asn | Pro | Ser | Pro | Ser |
| GAG | TAC | CCA | TCA | CAA | CCT | TCA | TCT | CCA | CCC | AAC | ACA |
| Glu | Tyr | Pro | Ser | Gln | Pro | Ser | Ser | Pro | Pro | Asn | Thr |
| AAA | AAA | AAA | AAA | AAA | AA | 935 | | | | | |
| | | | | | | CGC | ACC | GCT | AAG | ACA | TTA |
| | | | | | | Arg | Thr | Ala | Lys | Thr | Leu |
| | | | | | | ATA | TCA | TCG | TGC | TTA | TAT |
| | | | | | | Ile | Ser | Ser | Cys | Leu | Tyr |
| | | | | | | TCC | ATT | CTG | GCA | ATG | ATA |
| | | | | | | Ser | Ile | Leu | Ala | Met | Ile |
| | | | | | | ATA | GCC | TCG | GCA | AAC | CAC |
| | | | | | | Ile | Ala | Ser | Ala | Asn | His |
| | | | | | | ACA | AGC | CAG | ATC | AAG | AAC |
| | | | | | | Thr | Ser | Gln | Ile | Lys | Asn |
| | | | | | | GGA | ATC | AGT | CCC | TCT | AAT |
| | | | | | | Gly | Ile | Ser | Pro | Ser | Asn |
| | | | | | | GCT | TCA | ACA | ACA | CCA | GGA |
| | | | | | | Ala | Ser | Thr | Thr | Pro | Gly |
| | | | | | | AAA | AAC | ACA | ACA | ACA | ACT |
| | | | | | | Lys | Asn | Thr | Thr | Thr | Thr |
| | | | | | | CAA | AAC | AAA | CCA | CCA | AGC |
| | | | | | | Gln | Asn | Lys | Pro | Pro | Ser |
| | | | | | | TTT | GTA | CCC | TGC | AGC | ATA |
| | | | | | | Phe | Val | Pro | Cys | Ser | Ile |
| | | | | | | AGA | ATA | CCA | AAC | AAA | AAA |
| | | | | | | Arg | Ile | Pro | Asn | Lys | Lys |
| | | | | | | CCA | ACC | CTC | AAG | ACA | ACC |
| | | | | | | Pro | Thr | Leu | Lys | Thr | Thr |
| | | | | | | GAA | GTA | CCC | ACC | ACC | AAG |
| | | | | | | Glu | Val | Pro | Thr | Thr | Lys |
| | | | | | | AAC | ATC | ATA | ACT | ACA | CTA |
| | | | | | | Asn | Ile | Ile | Thr | Thr | Leu |
| | | | | | | AGT | CAA | ATG | GAA | ACC | TTC |
| | | | | | | Ser | Gln | Met | Glu | Thr | Phe |
| | | | | | | CAA | GTC | TCT | ACA | ACA | TCC |
| | | | | | | Gln | Val | Ser | Thr | Thr | Ser |
| | | | | | | CCA | CGC | CAG | TAG | TTA | CTT |
| | | | | | | Pro | Arg | Gln | End | | |

CHART 14

CHART 15

Complete nucleotide sequence of 22K mRNA and the predicted protein sequence encoded by the 5'-proximal open reading frame

| | | | | | | | | | | | | | | | |
|---|---|---|---|---|---|---|---|---|---|---|---|---|---|---|---|
| GGG | GCA | AAT | ATG | TCA | CGA | ACG | AAT | CCT | TGC | AAA | TTT | GAA | ATT | CGA | |
| | | | Met | Ser | Arg | Arg | Asn | Pro | Cys | Lys | Phe | Glu | Ile | Arg | |
| TTT | AGT | CAT | AAT | TAT | TTT | GAA | TGG | CCA | CCC | CAT | GCA | CTG | CTT | GTA | |
| Phe | Ser | His | Asn | Tyr | Phe | Glu | Trp | Pro | Pro | His | Ala | Leu | Leu | Val | |
| AAG | TCT | ATG | GAT | AAA | AGT | ATA | GAT | ACC | TTA | TCA | GAA | ATA | AGT | GGA | |
| Lys | Ser | Met | Asp | Lys | Ser | Ile | Asp | Thr | Leu | Ser | Glu | Ile | Ser | Gly | |
| GCT | CTT | GGT | GTA | GTT | GGA | GTG | CTA | GAG | AGT | TAT | ATA | GGA | TCA | ATA | |
| Ala | Leu | Gly | Val | Val | Gly | Val | Leu | Glu | Ser | Tyr | Ile | Gly | Ser | Ile | |
| GCC | ATG | AGC | AAA | CTC | CTC | ACT | GAA | CTC | AAT | AGT | GAT | GAT | ATC | AAA | |
| Ala | Met | Ser | Lys | Leu | Leu | Thr | Glu | Leu | Asn | Ser | Asp | Asp | Ile | Lys | |
| CCC | AAG | ATA | AGA | GTG | TAC | AAT | ACT | GTC | ATA | TCA | TAT | ATT | GAA | AGC | |
| Pro | Lys | Ile | Arg | Val | Tyr | Asn | Thr | Val | Ile | Ser | Tyr | Ile | Glu | Ser | |
| CTG | TTA | AAA | AGA | TTG | CCA | GCA | GAC | GTA | TTG | AAG | AAA | ACC | ATC | AAA | |
| Leu | Leu | Lys | Arg | Leu | Pro | Ala | Asp | Val | Leu | Lys | Lys | Thr | Ile | Lys | |
| ATC | AAC | AAC | CCA | AAA | GAA | TCA | ACT | GTT | AGT | GAT | ACA | AAT | GAC | CAT | |
| Ile | Asn | Asn | Pro | Lys | Glu | Ser | Thr | Val | Ser | Asp | Thr | Asn | Asp | His | |
| TCC | TTG | TAG | TAT | AAC | TTC | CAT | ACT | AAT | AAC | AAG | TAG | ATG | TAG | ACT | |
| TTT | CAA | TCA | AAA | CAA | CCC | AAA | TAA | CCA | TAT | GTA | CTC | ACC | GAA | TCA | |
| AGA | ATT | GAT | TGA | CAC | AAT | TCA | AAA | TTT | TCT | ACA | ACA | TCT | AGG | TAT | |
| AGT | GTC | ATA | ACA | CTC | AAT | TCT | AAC | ACT | CAC | CAC | ATC | GTT | ACA | TTA | |
| AAT | GGA | TCC | CAT | TAT | TAA | TGG | AAA | TTC | TGC | TAA | TGT | TTA | TCT | AAC | |
| | | | | | GGT | CAT | TGC | TTA | AAT | GGT | AAG | AGG | TGT | CAT | 75 |
| | | | | | Gly | His | Cyc | Leu | Asn | Gly | Lys | Arg | Cys | His | 22 |
| | | | | | AGA | CAA | AAC | TTT | ATG | TTA | AAC | AGA | ATA | CTT | 150 |
| | | | | | Arg | Gln | Asn | Phe | Met | Leu | Asn | Arg | Ile | Leu | 47 |
| | | | | | GCT | GCA | GAG | TTG | GAC | AGA | ACA | GAA | GAG | TAT | 225 |
| | | | | | Ala | Ala | Glu | Leu | Asp | Arg | Thr | Glu | Glu | Tyr | 72 |
| | | | | | AAC | AAT | ATA | ACT | AAA | CAA | TCA | GCA | TGT | GTT | 300 |
| | | | | | Asn | Asn | Ile | Thr | Lys | Gln | Ser | Ala | Cys | Val | 97 |
| | | | | | AAG | CTG | AGG | GAC | AAT | GAA | GAG | CTA | AAT | TCA | 375 |
| | | | | | Lys | Leu | Arg | Asp | Asn | Glu | Glu | Leu | Asn | Ser | 122 |
| | | | | | AAC | AGG | AAA | AAC | AAT | AAA | CAA | ACT | ATC | CAT | 450 |
| | | | | | Asn | Arg | Lys | Asn | Asn | Lys | Gln | Thr | Ile | His | 147 |
| | | | | | AAC | ACA | TTG | GAT | ATC | CAT | AAG | AGC | ATA | ACC | 525 |
| | | | | | Asn | Thr | Leu | Asp | Ile | His | Lys | Ser | Ile | Thr | 172 |
| | | | | | GCC | AAA | AAT | AAT | GAT | ACT | ACC | TGA | CAA | ATA | 600 |
| | | | | | Ala | Lys | Asn | Asn | Asp | Thr | Thr | | | | 194 |
| | | | | | TAC | TAT | CTA | TAA | TCA | AAA | GAA | CAC | ACT | ATA | 675 |
| | | | | | AAC | ATT | CAA | TGA | AAT | CCA | TTG | GAC | CTC | TCA | 750 |
| | | | | | TAT | TGA | GGA | TAT | ATA | TAC | AAT | ATA | TAT | ATT | 825 |
| | | | | | TTA | ATT | CAA | ACA | ATT | CAA | GTT | GTG | GGA | CAA | 900 |
| | | | | | CGA | TAG | TTA | TTT | | | | | | | 957 |

Complete nucleotide sequence of the 1A mRNA and the predicted amino acid sequence of the encoded protein

| | | | | | | | | | | | | |
|---|---|---|---|---|---|---|---|---|---|---|---|---|
| GGG | GCA | AAT | AAT | CAT | TGG | AGG | AAA | TCC | AAC | TAA | TCA | |
| CCA | CAC | ACC | ATA | CAG | AAT | CAA | CCA | ATG | GAA | AAT | ACA | |
| | | | | | | | | Met | Glu | Asn | Thr | |
| AAA | TTC | TGG | CCT | TAC | TTT | ACA | CTA | ATA | CAC | ATG | ATC | |
| Lys | Phe | Trp | Pro | Tyr | Phe | Thr | Leu | Ile | His | Met | Ile | |
| ATA | ATC | TCC | ATC | ATG | ATT | GCA | ATA | CTA | AAC | AAA | CTT | |
| Ile | Ile | Ser | Ile | Met | Ile | Ala | Ile | Leu | Asn | Lys | Leu | |
| AAA | ACC | TTT | GAG | TTA | CCA | AGA | GCT | CGA | GTC | AAC | ACA | |
| Lys | Thr | Phe | Glu | Leu | Pro | Arg | Ala | Arg | Val | Asn | Thr | |
| AAA | ACA | GTA | ACC | TTG | CAT | TTA | AAA | ATG | AAC | AAC | CCC | |
| CAT | CCC | ACC | ATG | CAA | ACC | ACT | ATC | CAT | ACT | ATA | AAG | |
| | | | | CAA | TAT | CTG | TTA | ACA | TAG | ACA | AGT | 60 |
| | | | | TCC | ATA | ACA | ATA | GAA | TTC | TCA | AGC | 120 |
| | | | | Ser | Ile | Thr | Ile | Glu | Phe | Ser | Ser | 12 |
| | | | | ACA | ACA | ATA | ATC | TCT | TTG | CTA | ATC | 180 |
| | | | | Thr | Thr | Ile | Ile | Ser | Leu | Leu | Ile | 32 |
| | | | | TGT | GAA | TAT | AAC | GTA | TTC | CAT | AAC | 240 |
| | | | | Cys | Glu | Tyr | Asn | Val | Phe | His | Asn | 52 |
| | | | | TAG | CAT | TCA | TCA | ATC | CAA | CAG | CCC | 300 |
| | | | | | | | | | | | | 64 |
| | | | | TAC | CTC | TTT | ACA | ACA | CCT | CAT | TAA | 360 |
| | | | | TAG | TTA | ATT | | | | | | 405 |

immunogenic fragments thereof.

2. A recombinant DNA molecule according to claim

CHART 16

Complete nucleotide sequence of the major nucleocapsid protein mRNA and the predicted amino acid sequence

| | | | | | | | | | | | | | | |
|---|---|---|---|---|---|---|---|---|---|---|---|---|---|---|
| GGG | GCA | AAT | ACA | AAG | ATG | GCT | CTT | AGC | AAA | GTC | AAG | TTG | AAT | GAT |
| | | | | | Met | Ala | Leu | Ser | Lys | Val | Lys | Leu | Asn | Asp |
| AGC | AAA | TAC | ACC | ATC | CAA | CGG | AGC | ACA | GGA | GAT | AGT | ATT | GAT | ACT |
| Ser | Lys | Tyr | Thr | Ile | Gln | Arg | Ser | Thr | Gly | Asp | Ser | Ile | Asp | Thr |
| AAG | TTA | TGT | GGC | ATG | TTA | TTA | ATC | ACA | GAA | GAT | GCT | AAT | CAT | AAA |
| Lys | Leu | Cys | Gly | Met | Leu | Leu | Ile | Thr | Glu | Asp | Ala | Asn | His | Lys |
| ATG | TCT | AGG | TTA | GGA | AGA | GAA | GAC | ACC | ATA | AAA | ATA | CTC | AGA | GAT |
| Met | Ser | Arg | Leu | Gly | Arg | Glu | Asp | Thr | Ile | Lys | Ile | Leu | Arg | Asp |
| GAT | GTA | ACA | ACA | CAT | CGT | CAA | GAC | ATT | AAT | GGA | AAA | GAA | ATG | AAA |
| Asp | Val | Thr | Thr | His | Arg | Gln | Asp | Ile | Asn | Gly | Lys | Glu | Met | Lys |
| ACT | GAA | ATT | CAA | ATC | AAC | ATT | GAG | ATA | GAA | TCT | AGA | AAA | TCC | TAC |
| Thr | Glu | Ile | Gln | Ile | Asn | Ile | Glu | Ile | Glu | Ser | Arg | Lys | Ser | Tyr |
| GCT | CCA | GAA | TAC | AGG | CAT | GAC | TCT | CCT | GAT | TGT | GGG | ATG | ATA | ATA |
| Ala | Pro | Glu | Tyr | Arg | His | Asp | Ser | Pro | Asp | Cys | Gly | Met | Ile | Ile |
| TTA | GCA | GCA | GGG | GAC | AGA | TCT | GGT | CTT | ACA | GCC | GTG | ATT | AGG | AGA |
| Leu | Ala | Ala | Gly | Asp | Arg | Ser | Gly | Leu | Thr | Ala | Val | Ile | Arg | Arg |
| CGT | TAC | AAA | GGC | TTA | CTA | CCC | AAG | GAC | ATA | GCC | AAC | AGC | TTC | TAT |
| Arg | Tyr | Lys | Gly | Leu | Leu | Pro | Lys | Asp | Ile | Ala | Asn | Ser | Phe | Tyr |
| GAT | GTT | TTT | GTT | CAT | TTT | GGT | ATA | GCA | CAA | TCT | TCT | ACC | AGA | GGT |
| Asp | Val | Phe | Val | His | Phe | Gly | Ile | Ala | Gln | Ser | Ser | Thr | Arg | Gly |
| TTG | TTT | ATG | AAT | GCC | TAT | GGT | GCA | GGG | CAA | GTG | ATG | TTA | CGG | TGG |
| Leu | Phe | Met | Asn | Ala | Tyr | Gly | Ala | Gly | Gln | Val | Met | Leu | Arg | Trp |
| ATG | TTA | GGA | CAT | GCT | AGT | GTG | CAA | GCA | GAA | ATG | GAA | CAA | GTT | GTT |
| Met | Leu | Gly | His | Ala | Ser | Val | Gln | Ala | Glu | Met | Glu | Gln | Val | Val |
| GGT | GAA | GCA | GGA | TTC | TAC | CAT | ATA | TTG | AAC | AAC | CCA | AAA | GCA | TCA |
| Gly | Glu | Ala | Gly | Phe | Tyr | His | Ile | Leu | Asn | Asn | Pro | Lys | Ala | Ser |
| TCC | AGT | GTA | GTA | TTA | GGC | AAT | GCT | GCT | GGC | CTA | GGC | ATA | ATG | GGA |
| Ser | Ser | Val | Val | Leu | Gly | Asn | Ala | Ala | Gly | Leu | Gly | Ile | Met | Gly |
| CTA | TAT | GAT | GCA | GCA | AAG | GCA | TAT | GCT | GAA | CAA | CTC | AAA | GAA | AAT |
| Leu | Tyr | Asp | Ala | Ala | Lys | Ala | Tyr | Ala | Glu | Gln | Leu | Lys | Glu | Asn |
| ACA | GCA | GAA | GAA | CTA | GAG | GCT | ATC | AAA | CAT | CAG | CTT | AAT | CCA | AAA |
| Thr | Ala | Glu | Glu | Leu | Glu | Ala | Ile | Lys | His | Gln | Leu | Asn | Pro | Lys |

| | | | | | | | | | | |
|---|---|---|---|---|---|---|---|---|---|---|
| ACA | CTC | AAC | AAA | GAT | CAA | CTT | CTG | TCA | TCC | 75 |
| Thr | Leu | Asn | Lys | Asp | Gln | Leu | Leu | Ser | Ser | 20 |
| CCT | AAT | TAT | GAT | GTG | CAG | AAA | CAC | ATC | AAT | 150 |
| Pro | Asn | Tyr | Asp | Val | Gln | Lys | His | Ile | Asn | 45 |
| TTC | ACT | GGG | TTA | ATA | GGT | ATG | TTA | TAT | GCG | 225 |
| Phe | Thr | Gly | Leu | Ile | Gly | Met | Leu | Tyr | Ala | 70 |
| GCG | GGA | TAT | CAT | GTA | AAA | GCA | AAT | GGA | GTA | 300 |
| Ala | Gly | Tyr | His | Val | Lys | Ala | Asn | Gly | Val | 95 |
| TTT | GAA | GTG | TTA | ACA | TTG | GCA | AGC | TTA | ACA | 375 |
| Phe | Glu | Val | Leu | Thr | Leu | Ala | Ser | Leu | Thr | 120 |
| AAA | AAA | ATG | CTA | AAA | GAA | ATC | GGA | GAG | GTA | 450 |
| Lys | Lys | Met | Leu | Lys | Glu | Met | Ala | Glu | Val | 145 |
| TTA | TGT | ATA | GCA | GCA | TTA | GTA | ATA | ACT | AAA | 525 |
| Leu | Cys | Ile | Ala | Ala | Leu | Val | Ile | Thr | Lys | 170 |
| GCT | AAT | AAT | GTC | CTA | AAA | AAT | GAA | ATG | AAA | 600 |
| Ala | Asn | Asn | Val | Leu | Lys | Asn | Glu | Met | Lys | 195 |
| GAA | GTG | TTT | GAA | AAA | CAT | CCC | CAC | TTT | ATA | 675 |
| Glu | Val | Phe | Glu | Lys | His | Pro | His | Phe | Ile | 220 |
| GGC | AGT | AGA | GTT | GAA | GGG | ATT | TTT | GCA | GGA | 750 |
| Gly | Ser | Arg | Val | Glu | Gly | Ile | Phe | Ala | Gly | 245 |
| GGA | GTC | TTA | GCA | AAA | TCA | GTT | AAA | AAT | ATT | 825 |
| Gly | Val | Leu | Ala | Lys | Ser | Val | Lys | Asn | Ile | 270 |
| GAG | GTT | TAT | GAA | TAT | GCC | CAA | AAA | TTG | GGT | 900 |
| Glu | Val | Tyr | Glu | Tyr | Ala | Gln | Lys | Leu | Gly | 295 |
| TTA | TTA | TCT | TTG | ACT | CAA | TTT | CCT | CAC | TTC | 975 |
| Leu | Leu | Ser | Leu | Thr | Gln | Phe | Pro | His | Phe | 320 |
| GAG | TAC | AGA | GGT | ACA | CCG | AGG | AAT | CAA | GAT | 1050 |
| Glu | Tyr | Arg | Gly | Thr | Pro | Arg | Asn | Gln | Asp | 345 |
| GGT | GTG | ATT | AAC | TAC | AGT | GTA | CTA | GAC | TTG | 1125 |
| Gly | Val | Ile | Asn | Tyr | Ser | Val | Leu | Asp | Leu | 370 |
| GAT | AAT | GAT | GTA | GAG | CTT | TGA | GTT | AAT | | 1197 |
| Asp | Asn | Asp | Val | Glu | Leu | | | | | 301 |

I claim:

1. A recombinant DNA molecule comprising a DNA sequence encoding human respiratory syncytial virus structural proteins selected from the group consisting of:

a) F protein;

b) G protein;

c) 22K protein;

d) 9.5K protein;

e) major capsid protein N; and

2. A recombinant DNA molecule according to claim 1 comprising a DNA sequence encoding human respiratory syncytial virus F protein or immunogenic fragments thereof.

3. A recombinant DNA molecule according to claim 1 comprising a DNA sequence encoding human respiratory syncytial virus F protein.

4. A recombinant DNA molecule according to claim 1 comprising a DNA sequence encoding human respiratory syncytial virus G protein or immunogenic fragments thereof.

5. A recombinant DNA molecule according to claim 4 comprising a DNA sequence encoding human respiratory syncytial virus G protein.

6. A recombinant DNA molecule according to claim 1 comprising a DNA sequence encoding human respiratory syncytial virus 22K protein or immunogenic fragments thereof.

7. A recombinant DNA molecule according to claim 6 comprising a DNA sequence encoding human respiratory syncytial virus 22K protein.

8. A recombinant DNA molecule according to claim 1 comprising a DNA sequence encoding human respiratory syncytial virus 9.5K protein or immunogenic fragments thereof.

9. A recombinant DNA molecule according to claim 8 comprising a DNA sequence encoding human respiratory syncytial virus 9.5K protein.

10. A recombinant DNA molecule according to claim 1 comprising a DNA sequence encoding human respiratory syncytial virus major capsid protein N or immunogenic fragments thereof.

11. A recombinant DNA molecule according to claim 10 comprising a DNA sequence encoding human respiratory syncytial virus major capsid protein N.

12. A recombinant DNA molecule according to claim 1 wherein said recombinant DNA molecule is a recombinant expression vector.

13. A recombinant expression vector according to claim 12 wherein said recombinant expression vector is functional in a host cell selected from the group consisting of:

a) bacteria;

b) yeast; and c) eukaryotic cell culture.

14. A recombinant expression vector according to claim 13 wherein said host cell is a bacteria cell.

15. A recombinant expression vector according to claim 13 wherein said host cell is a yeast cell.

16. A recombinant expression vector according to claim 13 wherein said host cell is a eukaryotic cell culture cell.

17. A recombinant expression vector according to claim 16 wherein said eukaryotic cell culture cell is an insect cell culture cell.

18. A recombinant expression vector according to claim 17 wherein said recombinant expression vector is a recombinant baculovirus.

19. A recombinant expression vector according to claim 18 wherein said recombinant vector is a recombinant Autographa Californica nuclear polyhedral virus.

20. A host cell comprising a recombinant expression vector according to claim 12, wherein said host cell is selected from the group consisting of:

a) bacteria;

b) yeast; and c) eukaryotic cell culture.

21. A host cell according to claim 20 wherein said host cell is a bacteria cell.

22. A host cell according to claim 20 wherein said host cell is a yeast cell.

23. A host cell according to claim 20 wherein said host cell is a eukaryotic cell culture cell.

24. A host cell according to claim 23 wherein said eukaryotic cell culture cell is an insect cell culture cell.

25. A host cell according to claim 24 wherein said recombinant expression vector is a recombinant baculovirus.

26. A host cell according to claim 25 wherein said recombinant baculovirus is a recombinant Autographa Californica nuclear polyhedral virus.

* * * * *